United States Patent
Bindra et al.

(10) Patent No.: US 9,233,948 B2
(45) Date of Patent: Jan. 12, 2016

(54) PHARMACEUTICAL COMPOSITIONS COMPRISING N-(4-(2-AMINO-3-CHLOROPYRIDIN-4-YLOXY)-3-FLUOROPHENYL)-4-ETHOXY-1-(4-FLUOROPHENYL)-2-OXO-1,2-DIHYDROPYRIDINE-3-CARBOXAMIDE

(71) Applicant: Bristol-Myers Squibb Company, Princeton, NJ (US)

(72) Inventors: Dilbir S. Bindra, New Brunswick, NJ (US); Madhushree Yeshwant Gokhale, New Brunswick, NJ (US); Cletus John Nunes, New Brunswick, NJ (US); Ajit B. Thakur, East Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/486,139

(22) Filed: Sep. 15, 2014

(65) Prior Publication Data

US 2015/0065719 A1 Mar. 5, 2015

Related U.S. Application Data

(62) Division of application No. 13/643,561, filed as application No. PCT/US2011/034417 on Apr. 29, 2011, now Pat. No. 8,911,785.

(60) Provisional application No. 61/329,710, filed on Apr. 30, 2010.

(51) Int. Cl.
| | | |
|---|---|---|
| *A61P 35/00* | (2006.01) | |
| *C07D 213/82* | (2006.01) | |
| *A61K 31/444* | (2006.01) | |
| *C07D 401/12* | (2006.01) | |

(52) U.S. Cl.
CPC ............ *C07D 401/12* (2013.01); *C07D 213/82* (2013.01)

(58) Field of Classification Search
None
See application file for complete search history.

(56) References Cited

U.S. PATENT DOCUMENTS

| | | | |
|---|---|---|---|
| 7,459,562 B2 | 12/2008 | Borzilleri et al. | |
| 7,851,489 B2 | 12/2010 | Borzilleri et al. | |
| 8,536,200 B2 | 9/2013 | Borzilleri et al. | |
| 2008/0114033 A1 | 5/2008 | Borzilleri et al. | |
| 2008/0260837 A1 | 10/2008 | Namburi et al. | |
| 2009/0111872 A1 | 4/2009 | Embrechts et al. | |

FOREIGN PATENT DOCUMENTS

WO    WO 2009/094427    7/2009

OTHER PUBLICATIONS

Slemon, Kilomentor Blog (2008), pp. 1-6 accessed at http://www.kilomentor.com/2008/06/ phosphate-pharmaceutical-salts-chemical-process-development-and-organic-synthesis Mar. 30, 2015.*

Schroeder, G.M. et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem., vol. 52, No. 5, pp. 1251-1254 (2009).

Vasconcelos, T., et al., "Solid dispersions as strategy to improve oral bioavailability of poor water soluble drugs," Drug Discovery Today, vol. 12, Nos. 23-24, pp. 1068-1075 (2007).

International Preliminary Report on Patentability issued Nov. 6, 2012.

Zimmerman, et al., (2006) accessed at (http://kuscholarworks.ku.edu/dspace/bitstream/1808/1801/1/PA24_Zimmermann.pdf) on Oct. 28, 2013.

* cited by examiner

*Primary Examiner* — Bethany Barham
*Assistant Examiner* — Lisbeth C Robinson
(74) *Attorney, Agent, or Firm* — Gary D. Greenblatt

(57) ABSTRACT

Disclosed are salts and crystalline forms of N-(4-(2-amino-3-chloropyridin-4-yloxy)-3-fluorophenyl)-4-ethoxy-1-(4-fluorophenyl)-2-oxo-1,2-dihydropyridine-3-carboxamide and salts thereof. Also disclosed are at least one pharmaceutical composition comprising at least one crystalline form of N-(4-(2-amino-3-chloropyridin-4-yloxy)-3-fluorophenyl)-4-ethoxy-1-(4-fluorophenyl)-2-oxo-1,2-dihydropyridine-3-carboxamide, at least one method of using at least one crystalline form of N-(4-(2-amino-3-chloropyridin-4-yloxy)-3-fluorophenyl)-4-ethoxy-1-(4-fluorophenyl)-2-oxo-1,2-dihydropyridine-3-carboxamide to treat cancer and/or other proliferative diseases, and processes to prepare crystalline forms of N-(4-(2-amino-3-chloropyridin-4-yloxy)-3-fluorophenyl)-4-ethoxy-1-(4-fluorophenyl)-2-oxo-1,2-dihydropyridine-3-carboxamide and salts thereof.

1 Claim, 17 Drawing Sheets

PHARMACEUTICAL COMPOSITIONS COMPRISING N-(4-(2-AMINO-3-CHLOROPYRIDIN-4-YLOXY)-3-FLUOROPHENYL)-4-ETHOXY-1-(4-FLUOROPHENYL)-2-OXO-1,2-DIHYDROPYRIDINE-3-CARBOXAMIDE

CROSS-REFERENCE TO RELATED APPLICATIONS

This application is a divisional application of U.S. patent application Ser. No. 13/643,561, filed Oct. 26, 2012, which is a national phase of International Patent Application No. PCT/US2011/034417, filed Apr. 29, 2011, which claims priority to provisional application, U.S. Ser. No. 61/329,710 filed on Apr. 30, 2010 incorporated by reference herein in their entirety.

DESCRIPTION

The present invention generally relates to pharmaceutical compositions comprising N-(4-(2-amino-3-chloropyridin-4-yloxy)-3-fluorophenyl)-4-ethoxy-1-(4-fluorophenyl)-2-oxo-1,2-dihydropyridine-3-carboxamide and salts thereof, and methods of using said pharmaceutical compositions to treat cancer and/or other proliferative diseases. Also disclosed are crystalline forms of N-(4-(2-amino-3-chloropyridin-4-yloxy)-3-fluorophenyl)-4-ethoxy-1-(4-fluorophenyl)-2-oxo-1,2-dihydropyridine-3-carboxamide and processes to prepare crystalline forms of N-(4-(2-amino-3-chloropyridin-4-yloxy)-3-fluorophenyl)-4-ethoxy-1-(4-fluorophenyl)-2-oxo-1,2-dihydropyridine-3-carboxamide.

Met, also referred to as hepatocyte growth factor receptor (HGFR), is expressed predominantly in epithelial cells but has also been identified in endothelial cells, myoblasts, hematopoietic cells and motor neurons. Overexpression of hepatocyte growth factor and activation of Met has been associated with the onset and progression in a number of different tumor types as well as in the promotion of metastatic disease.

The compound, N-(4-(2-Amino-3-chloropyridin-4-yloxy)-3-fluorophenyl)-4-ethoxy-1-(4-fluorophenyl)-2-oxo-1,2-dihydropyridine-3-carboxamide, has the structure of Formula (I):

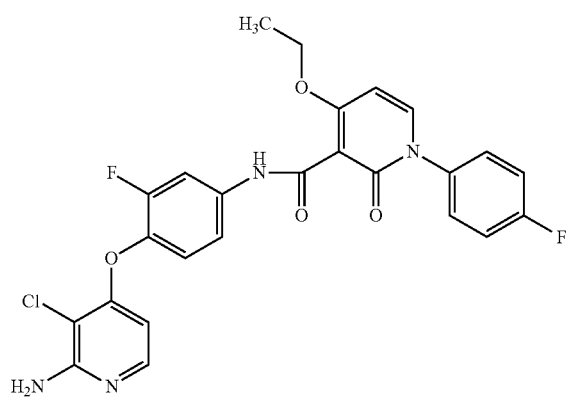

(I)

and is referred to herein as "Compound (I)". Compound (I), a process to prepare Compound (I), and methods of treatment employing Compound (I) are disclosed in U.S. Patent Application Publication No. 2008/0114033 A1. This reference is assigned to the present assignee and is incorporated herein by reference in its entirety. WO 2009/094427 (PCT/US2009/031665) also discloses a process to prepare Compound (I).

Compound (I) is useful for treating Met-related cancers. However, before Compound (I) is used to treat diseases in patients, it must be formulated into a pharmaceutical composition that can be administered to the patient; for example, into a dosage form suitable for oral, mucosal, parenteral, or transdermal administration. Formulations for oral administration are preferred since they are more convenient and easier to administer than other formulations. Also, the oral route of administration avoids the pain and discomfort of parenteral administration. Accordingly, formulations for oral administration are preferred by patients, and typically result in better patient compliance with dosing schedules.

Typically, in preparing a pharmaceutical composition, a form of the active ingredient is sought that has a balance of desired properties, such as, for example, dissolution rate, solubility, bioavailability, and/or storage stability. For example, a form of the active ingredient is sought having sufficient stability, solubility, and bioavailability to prevent the sufficiently soluble and bioavailable form from converting during the manufacture, preparation, and/or storage of the pharmaceutical composition to another form having an undesirable solubility and/or bioavailability profile. In addition, a form of the active ingredient may also be sought that permits the active ingredient to be isolated and/or purified during, for example, a preparative process.

The present invention provides at least one form of Compound (I) that surprisingly affords a balance of properties sought in a pharmaceutical composition. The present invention is also directed to other important aspects.

SUMMARY OF THE INVENTION

Described herein is a first crystalline form of Compound (I):

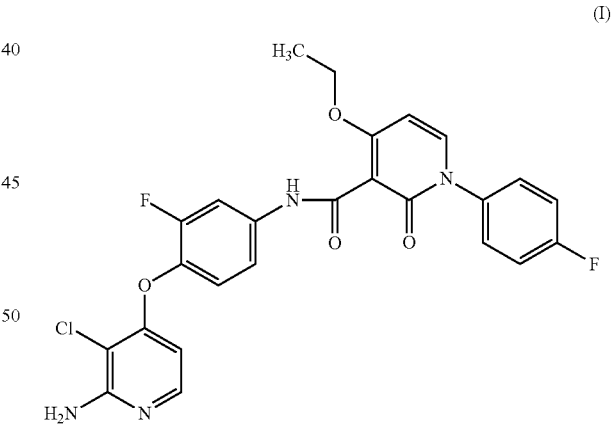

(I)

comprising Form N-1.

Described is a second crystalline form of Compound (I) comprising Form H1.5-2.

Described is a first crystalline form of a mono-hydrochloric acid salt of Compound (I) comprising Form H-1.

Described is a second crystalline form of a mono-hydrochloric acid salt of Compound (I) comprising Form N-2.

Described is a phosphoric acid salt of Compound (I).

Further described herein is at least one pharmaceutical composition comprising at least one crystalline form of Compound (I) and at least one pharmaceutically acceptable carrier and/or diluent.

Even further described herein is at least one method for treating cancer and/or other proliferative diseases, comprising administering to a patient in need thereof, an amount of Compound (I), wherein Compound (I) or a salt thereof is provided as a crystalline form.

BRIEF DESCRIPTION OF THE DRAWINGS

The invention is illustrated by reference to the accompanying drawings described below.

DETAILED DESCRIPTION OF THE INVENTION

Figure 1:
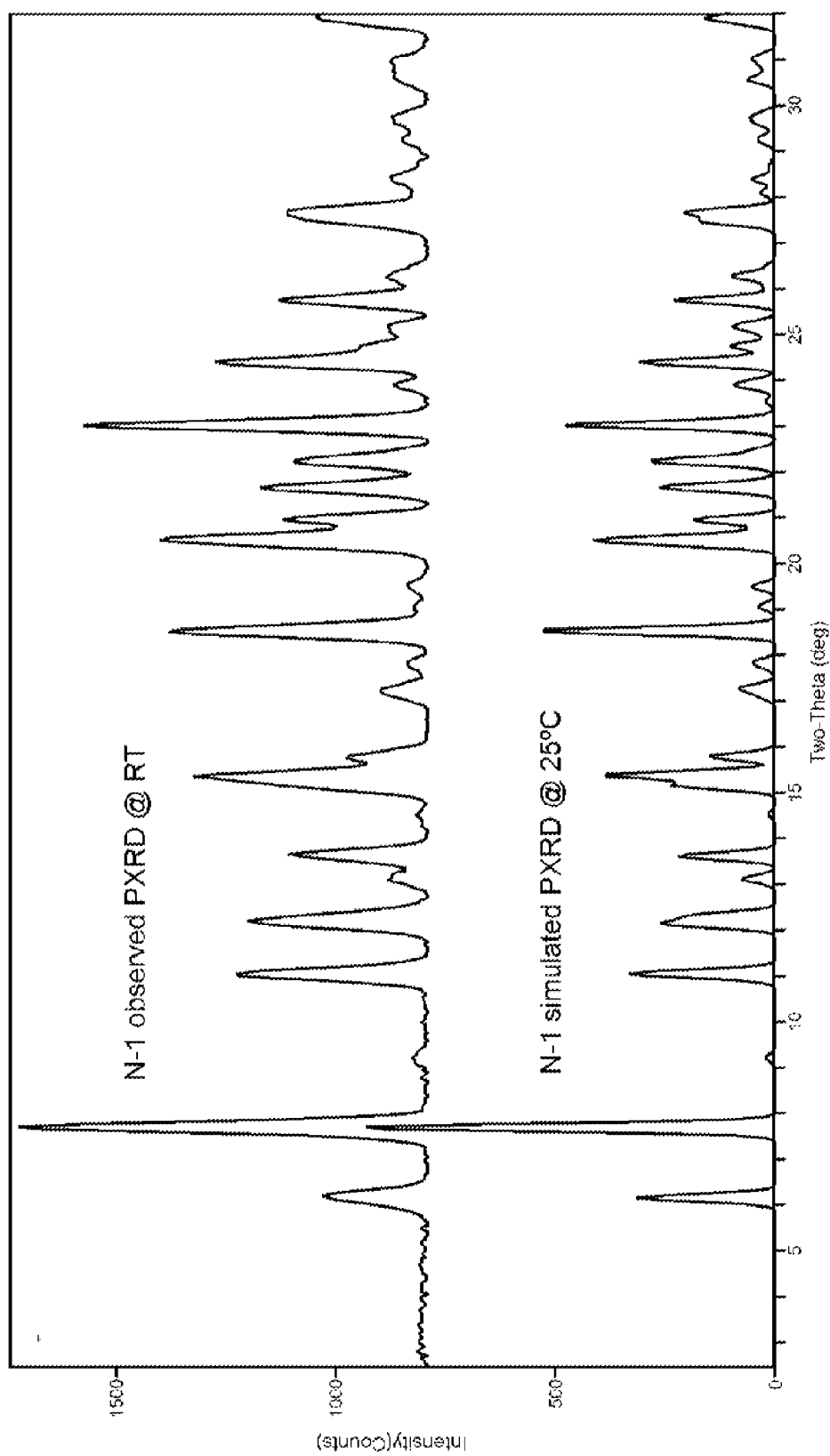
FIG. 1 shows observed (at room temperature (r.t.)) and simulated (at a Temperature (T) of about 25° C.) powder x-ray diffraction (PXRD) patterns (CuKα λ=1.5418 Å) of the N-1 Form of Compound (I).

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g., "N-1" etc., are merely identifiers that are to be interpreted in accordance with the characterization information presented herein and are not to be limited so as to exclude any other substance possessing similar or identical physical and chemical characteristics.

The definitions set forth herein take precedence over definitions set forth in any patent, patent application, and/or patent application publication incorporated herein by reference.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

As used herein, "polymorphs" refer to crystalline forms having the same chemical structure but different spatial arrangements of the molecules and/or ions forming the crystals.

As used herein, "amorphous" refers to a solid form of a molecule and/or ion that is not crystalline. An amorphous solid does not display a definitive X-ray diffraction pattern with sharp maxima.

As used herein, the term "substantially pure" means the crystalline form of Compound (I) referred to contains at least about 90 wt. %, based on the weight of such crystalline form, of a form selected from Form N-1 and Form H1.5-2. The term "at least about 90 wt. %," while not intending to limit the applicability of the doctrine of equivalents to the scope of the claims, includes, but is not limited to, for example, about 90, 90, about 91, 91, about 92, 92, about 93, 93, about 94, 94, about 95, 95, about 96, 96, about 97, 97, about 98, 98, about 99, 99, and about 100 wt. %, based on the weight of the crystalline form referred to. The remainder of the crystalline form of Compound (I) may comprise other Form(s) of Compound (I) and/or reaction impurities and/or processing impurities that arise, for example, when the crystalline form is prepared.

For example, a crystalline form of Compound (I) may be deemed substantially pure if the crystalline form contains at least 90 wt. %, based on the weight of such crystalline form as measured by means that are at this time known and generally accepted in the art, of a Form selected from Form N-1 and Form H1.5-2; and less than about 10 wt. %, based on the weight of such crystalline form, of material comprising other Form(s) of Compound (I) and/or reaction impurities and/or processing impurities.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the parameter "molecules/asymmetric unit" refers to the number of molecules of Compound (I) in the asymmetric unit.

As used herein, the unit cell parameter "molecules/unit cell" refers to the number of molecules of Compound (I) in the unit cell.

When dissolved, the crystalline form of Compound (I) loses its crystalline structure, and is therefore referred to as a solution of Compound (I). At least one crystalline form of Compound (I) disclosed herein may be used to prepare at least one liquid formulation in which at least one crystalline form of Compound (I) is dissolved and/or suspended.

By "therapeutically effective amount" is meant an amount that when administered either alone, or in combination with an additional therapeutic agent is effective to prevent, suppress, and/or ameliorate a disease and/or condition and/or the progression of a disease and/or condition. For example, effective anticancer agents prolong the survivability of the patient, inhibit the rapidly proliferating cell growth associated with the neoplasm, or effect a regression of the neoplasm.

The phrase "gene amplification," as used herein means the selective synthesis of a DNA fragment that results in multiple copies of the Met gene or fragment of the chromosome in which Met is encoded.

The phrase "activated Met mutation" as used herein means a selective change in the DNA sequence of Met resulting in a Met protein that is constitutively (i.e., permanently) phosphorylated.

The phrase "HGF stimulation," as used herein means the ability of HGF to bind its cognate receptor (Met) in such a way as to activate the receptor that results in a phenotypic response. In the case of Met, this can be cellular proliferation, motility, differentiation and/or survival.

The term "patient" as used herein encompasses all mammalian species, including humans, cows, horses, dogs, and cats.

Crystalline forms of Compound (I) and salts are shown in Table 1.

TABLE 1

| Compound (I) | Form |
|---|---|
| free base | N-1 |
| free base sesquihydrate | H1.5-2 |
| HCl monohydrate salt | H-1 |
| HCl salt | N-2 |
| H$_3$PO$_4$ salt | — |

Form N-1

A first crystalline form of Compound (I) comprises a neat crystalline form referred to herein as "Form N-1" or "N-1 Form".

In one embodiment, the N-1 Form is characterized by unit cell parameters approximately equal to the following:
Cell dimensions:
a=14.45 Å
b=19.21 Å
c=8.89 Å
α=90.0°
β=95.7°
γ=90.0°
Space group: P2$_1$/c
Molecules of Compound (I)/asymmetric unit: 1
Volume=636 Å$^3$
Density (calculated)=1.388 g/cm$^3$,
wherein the unit cell parameters of Form N-1 are measured at a temperature of about 25° C.

In one embodiment, the N-1 Form is characterized by unit cell parameters approximately equal to the following:
Cell dimensions:
a=14.43 Å
b=19.17 Å
c=8.83 Å
α=90.0°
β=95.4°
γ=90.0°
Space group: P2$_1$/c
Molecules of Compound (I)/asymmetric unit: 1
Volume=608 Å$^3$
Density (calculated)=1.401 g/cm$^3$,
wherein the unit cell parameters of Form N-1 are measured at a temperature of about −30° C.

In another embodiment, the N-1 Form is characterized by a simulated PXRD pattern substantially in accordance with the pattern shown in FIG. 1 and/or by an observed PXRD pattern substantially in accordance with the pattern shown in FIG. 1.

In yet another embodiment, the N-1 Form is characterized by a PXRD pattern (CuKα λ=1.5418 Å at a temperature of about 25° C.) comprising four or more, preferably five or more, 2θ values (CuKα λ=1.5418 Å) selected from: 6.2±0.2; 7.7±0.2; 11.0±0.2; 12.2±0.2; 18.5±0.2; 21.6±0.2; 22.2±0.2; and 23.0±0.2, wherein the PXRD pattern of Form N-1 is measured at a temperature of about 25° C.

In yet an even further embodiment, the N-1 Form is characterized by fractional atomic coordinates substantially as listed in Table 2.

TABLE 2

Fractional Atomic Coordinates for Form N-1
Calculated at a Temperature of About 25° C.

| Atom | X | Y | Z |
|---|---|---|---|
| Cl1 | −0.25879 | 0.54806 | 0.19187 |
| O2 | 0.21275 | 0.09822 | 0.63720 |
| N3 | −0.39114 | 0.44642 | 0.49461 |
| N4 | 0.16557 | 0.28605 | 0.57700 |
| O5 | 0.36855 | 0.31217 | 0.64881 |
| N7 | −0.43488 | 0.53891 | 0.33760 |
| C8 | 0.21176 | 0.23135 | 0.52660 |
| O9 | −0.13634 | 0.43919 | 0.31710 |
| O10 | 0.19309 | 0.20449 | 0.40331 |
| C11 | 0.28846 | 0.20478 | 0.63751 |
| N6 | 0.43110 | 0.22297 | 0.79501 |
| C12 | 0.36144 | 0.25108 | 0.69081 |
| C13 | −0.36963 | 0.49202 | 0.38770 |
| C14 | −0.28286 | 0.48942 | 0.32891 |
| C15 | 0.28651 | 0.13671 | 0.68670 |
| C16 | −0.32784 | 0.39900 | 0.54240 |
| C17 | 0.42909 | 0.15513 | 0.83881 |
| C18 | 0.08868 | 0.32198 | 0.50640 |
| C19 | −0.21905 | 0.43952 | 0.38130 |
| C20 | 0.50799 | 0.26667 | 0.85370 |
| C21 | −0.24117 | 0.39288 | 0.49180 |
| F22 | 0.72599 | 0.38614 | 1.02611 |
| C23 | −0.06396 | 0.39867 | 0.38541 |
| C24 | 0.59731 | 0.24605 | 0.83710 |
| F25 | −0.06998 | 0.33052 | 0.16930 |
| C26 | 0.36088 | 0.11125 | 0.78791 |
| C27 | 0.49111 | 0.32781 | 0.92870 |
| C28 | −0.02143 | 0.41399 | 0.52711 |
| C29 | −0.02883 | 0.34571 | 0.30741 |
| C30 | 0.05369 | 0.37612 | 0.58710 |
| C31 | 0.65331 | 0.34642 | 0.96870 |
| C32 | 0.04657 | 0.30717 | 0.36490 |
| C33 | 0.67162 | 0.28612 | 0.89630 |
| C34 | 0.56491 | 0.36857 | 0.98620 |
| C35 | 0.20439 | 0.02824 | 0.69211 |
| C36 | 0.11488 | −0.00020 | 0.61721 |
| F37 | −0.05473 | 0.45723 | 0.59400 |
| H33 | 0.73439 | 0.27211 | 0.88590 |
| H24 | 0.60718 | 0.20364 | 0.78383 |
| H27 | 0.42861 | 0.34175 | 0.94169 |
| H34 | 0.55268 | 0.41157 | 1.03560 |
| H17 | 0.47747 | 0.13662 | 0.90936 |
| H26 | 0.36196 | 0.06342 | 0.81942 |
| H35A | 0.25666 | 0.00131 | 0.66708 |

TABLE 2-continued

Fractional Atomic Coordinates for Form N-1
Calculated at a Temperature of About 25° C.

| Atom | X | Y | Z |
|---|---|---|---|
| H35B | 0.20365 | 0.02963 | 0.79998 |
| H36A | 0.10541 | −0.04704 | 0.65016 |
| H36B | 0.11740 | 0.00027 | 0.50966 |
| H36C | 0.06440 | 0.02858 | 0.64256 |
| H4 | 0.18518 | 0.30537 | 0.67457 |
| H32 | 0.06920 | 0.26925 | 0.30854 |
| H30 | 0.08190 | 0.38654 | 0.68697 |
| H21 | −0.19892 | 0.35762 | 0.53298 |
| H16 | −0.34175 | 0.36600 | 0.61810 |
| H7A | −0.42210 | 0.57221 | 0.26187 |
| H7B | −0.49425 | 0.53888 | 0.37741 |
| H28 | −0.04457 | 0.45146 | 0.58425 |
| H29 | −0.05781 | 0.33479 | 0.20830 |

Figure 6:
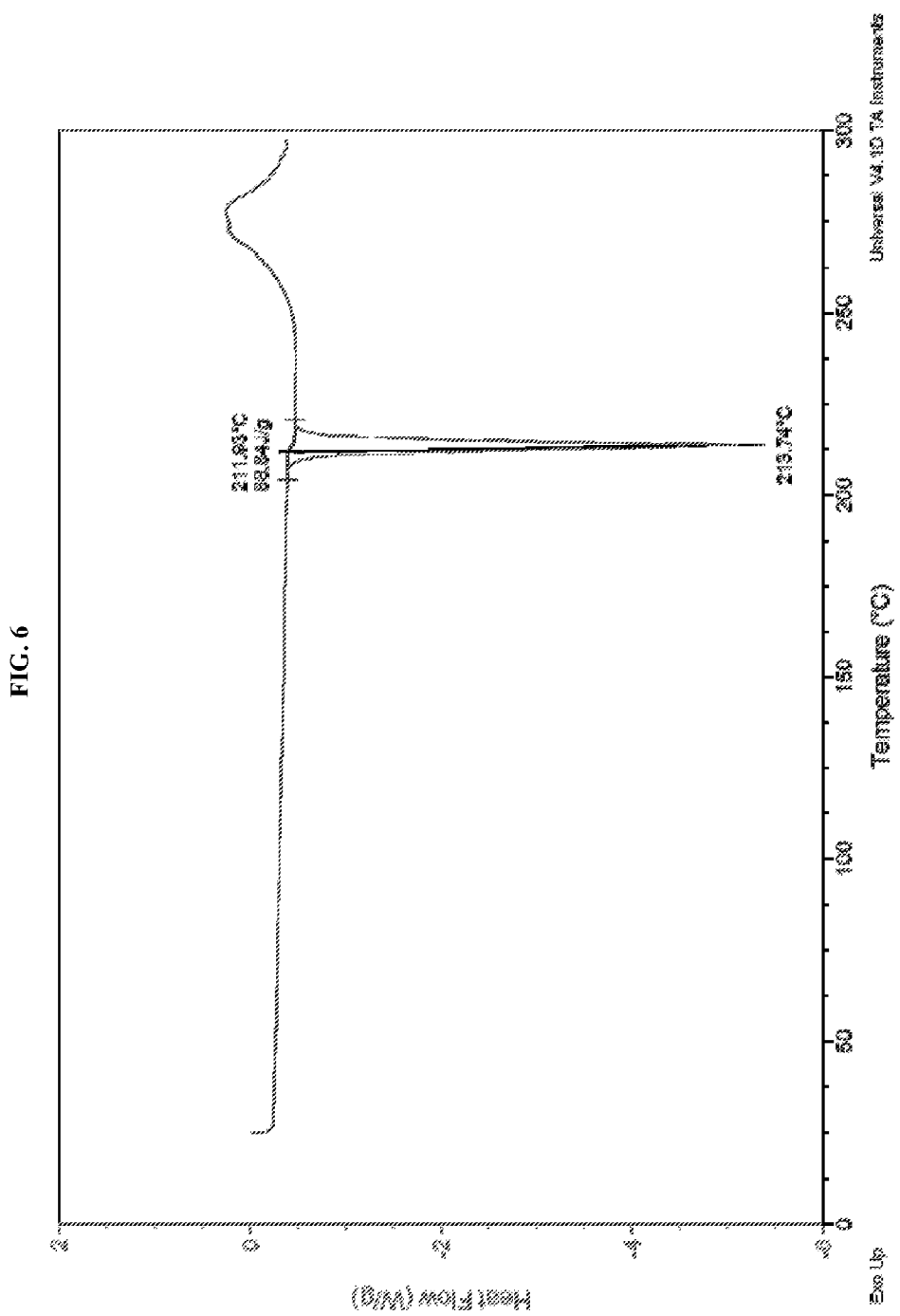
FIG. 6 shows a differential scanning calorimetry (DSC) thermogram of the N-1 Form of Compound (I).

In a still further embodiment, the N-1 Form is characterized by a DSC thermogram substantially in accordance with that shown in FIG. 6. The N-1 Form may be characterized by a melting point in the range of from about 211° C. to about 217° C.

In still another embodiment, the N-1 Form is characterized by a TGA thermogram, wherein the N-1 Form experiences either no weight loss or minimal weight loss upon being heated to a temperature of about 175° C.

Figure 11:
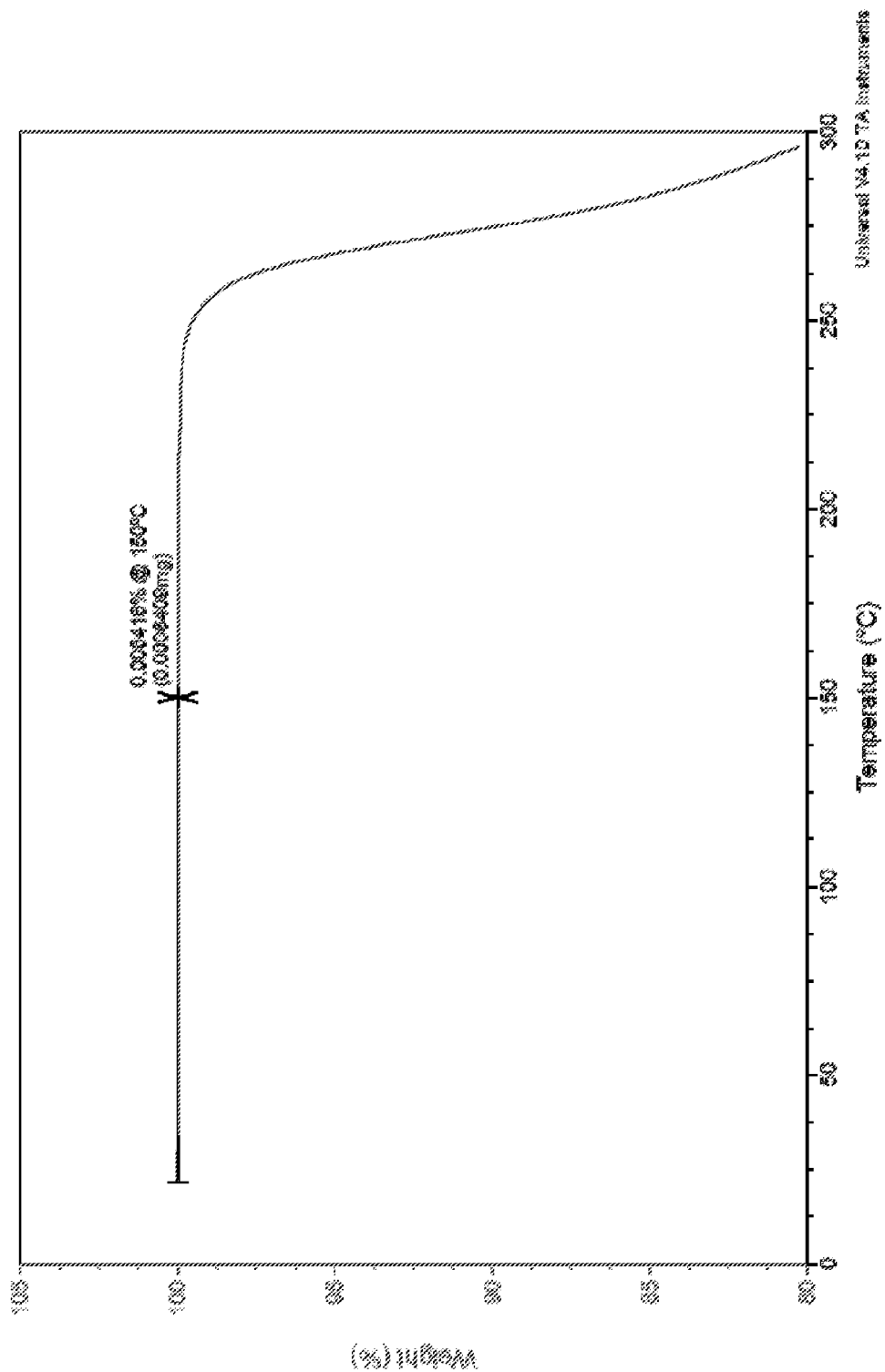
FIG. 11 shows a thermogravimetric analysis (TGA) thermogram of the N-1 Form of Compound (I).

In still an even further embodiment, the N-1 Form exhibits a TGA thermogram substantially the same as shown in FIG. 11.

Figure 16:
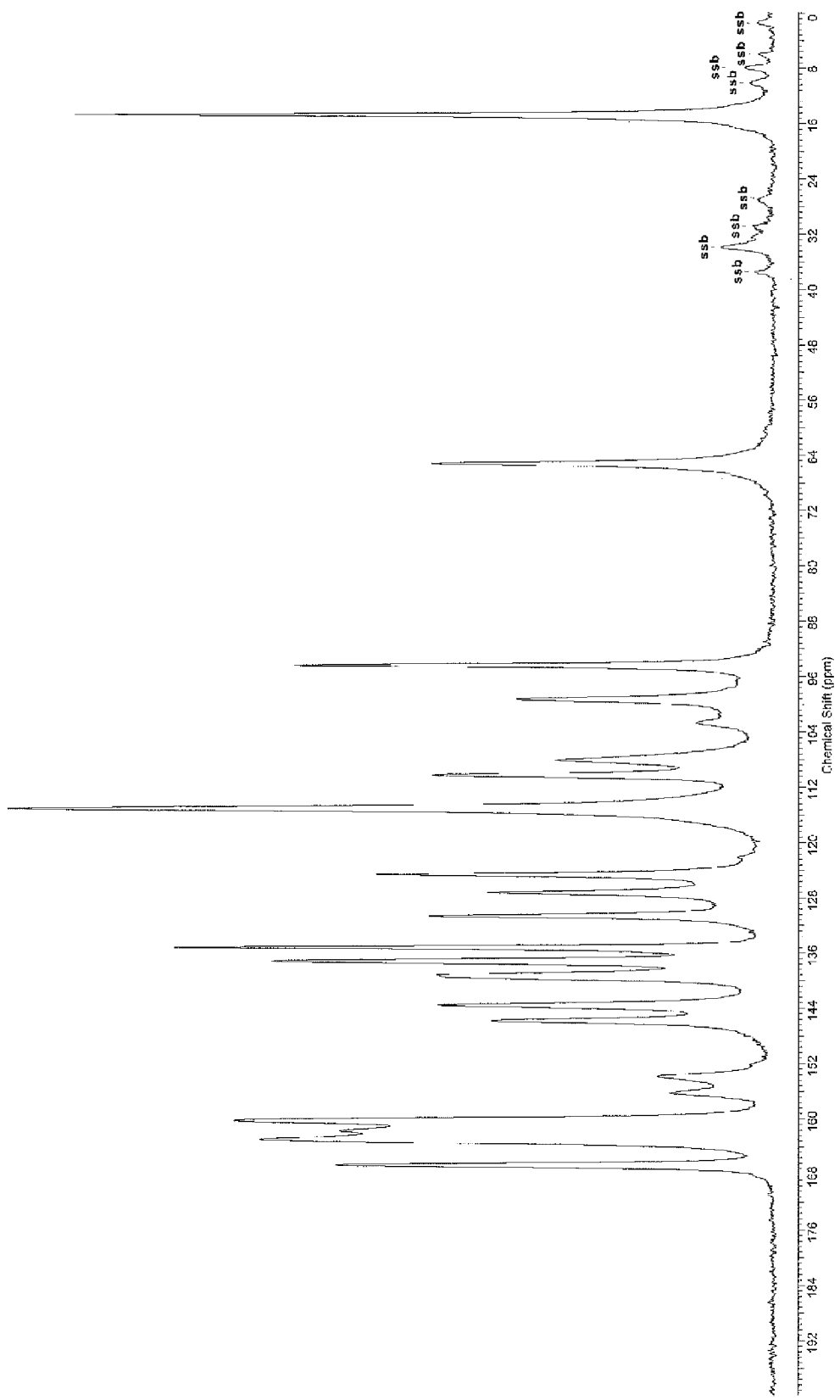
FIG. 16 shows the solid state nuclear magnetic resonance spectra (ssNMR) of the N-1 Form of Compound (I).

In another embodiment, the N-1 Form is characterized by a solid state nuclear magnetic resonance spectra (ssNMR) substantially in accordance with the spectra shown in FIG. 16.

In still yet another embodiment, the first crystalline form of Compound (I) is substantially pure.

In still yet an even further embodiment, the first crystalline form of Compound (I) contains at least about 90 wt. %, preferably at least about 95 wt. %, and more preferably at least about 99 wt. %, based on weight of the first crystalline form, Form N-1.

In a still further embodiment, a substantially pure first crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure first crystalline form has substantially pure phase homogeneity with less than about 1% of the total peak area of the experimentally measured PXRD pattern arising from peaks that are absent from the simulated PXRD pattern.

In another embodiment, the first crystalline form of Compound (I) consists essentially of Form N-1. The first crystalline form of this embodiment may comprise at least about 90 wt. %, preferably at least about 95 wt. %, and more preferably at least about 99 wt. %, based on the weight of the first crystalline form, Form N-1.

In yet another embodiment, a pharmaceutical composition comprises a first crystalline form; and at least one pharmaceutically-acceptable carrier and/or diluent.

In still another embodiment, a pharmaceutical composition comprises substantially pure Form N-1; and at least one pharmaceutically-acceptable carrier and/or diluent.

In still an even further embodiment, a therapeutically effective amount of Form N-1 is combined with at least one pharmaceutically acceptable carrier and/or diluent to provide at least one pharmaceutical composition.

Still yet a further embodiment provides a method for treating a proliferative disease comprising administering to a patient in need thereof, a therapeutically effective amount of Compound (I), wherein Compound (I) is provided in a first crystalline form comprising Form N-1. Preferably, the patient is a human. The method of this embodiment can be used to treat proliferative diseases selected from bladder cancer, breast cancer, colorectal cancer, gastric cancer, head and neck cancer, kidney cancer, liver cancer, lung cancer, ovarian cancer, pancreas/gallbladder cancer, prostate cancer, thyroid cancer, osteosarcoma, rhabdomyosarcoma, glioblastomas/astrocytomas, melanoma, MFH/fibrosarcoma, and mesothelioma; and preferably, lung cancer, head and neck cancer, gastric cancer, or bladder cancer.

In an even further embodiment, the method comprises administering Compound (I) wherein Compound (I) consists essentially of Form N-1.

Form H1.5-2

A second crystalline form of Compound (I) comprises a sesquihydrate crystalline form referred to herein as "Form H1.5-2" or "H1.5-2 Form". The sesquihydrate Form H1.5-2 comprises up to 1.5 molecules of water for each molecule of Compound (I).

In one embodiment, the H1.5-2 Form is characterized by unit cell parameters approximately equal to the following:
Cell dimensions:
a=11.62 Å
b=23.86 Å
c=9.09 Å
α=90.0°
β=84.4°
γ=90.0°
Space group: $P2_1/c$
Molecules of Compound (I)/asymmetric unit: 1
Volume=627 Å$^3$
Density (calculated)=1.430 g/cm$^3$,
wherein the unit cell parameters of Form H1.5-2 are measured at a temperature of about −30° C.

Figure 2:
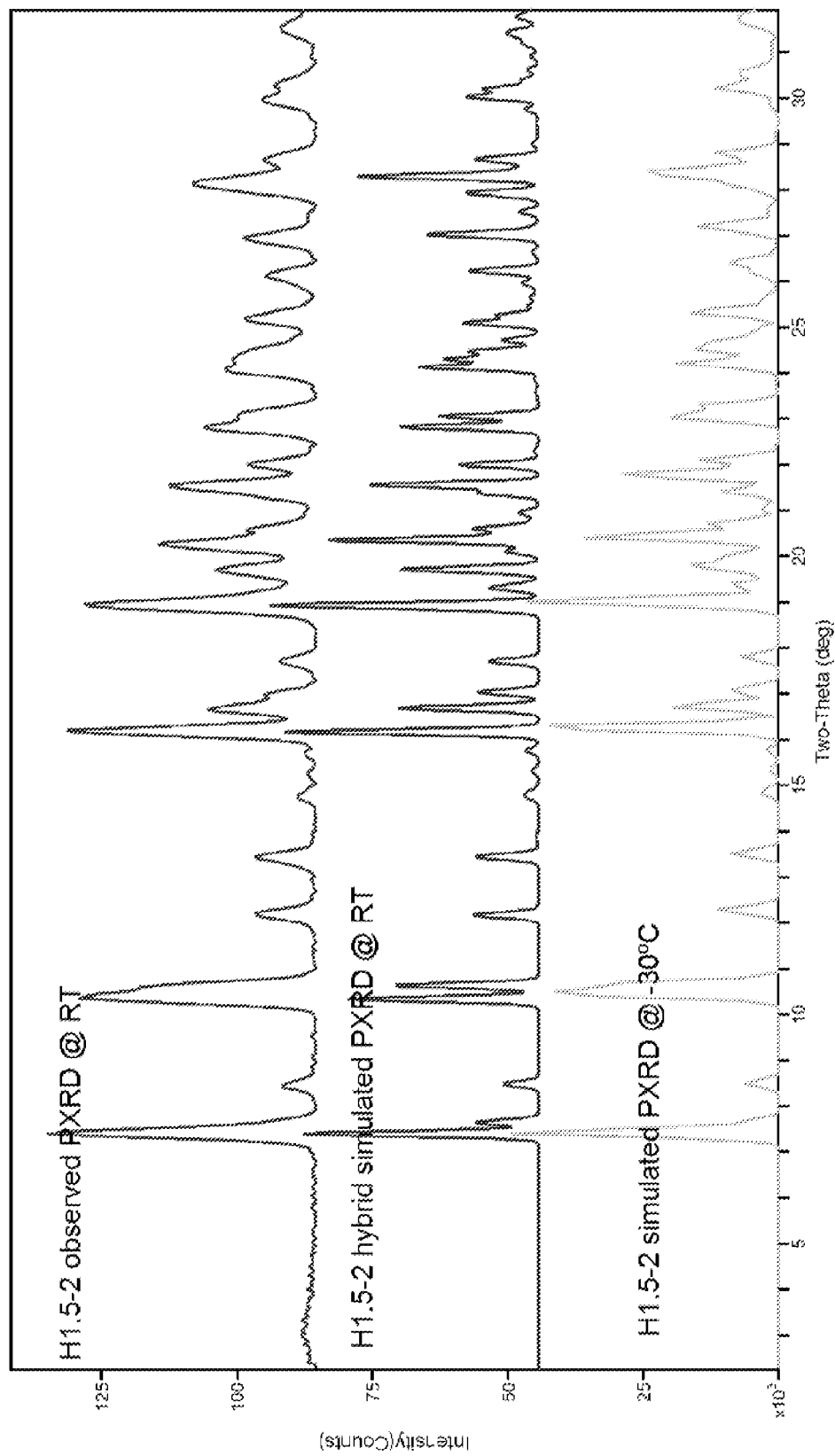
FIG. 2 shows observed (at r.t.), hybrid simulated (at r.t.), and simulated (at about −30° C.) PXRD patterns (CuKα λ=1.5418 Å) of the H1.5-2 Form of Compound (I).

In another embodiment, the H1.5-2 Form is characterized by a simulated powder x-ray diffraction (PXRD) pattern substantially in accordance with the pattern shown in FIG. 2 and/or by an observed PXRD pattern substantially in accordance with the pattern shown in FIG. 2.

In yet another embodiment, the H1.5-2 Form is characterized by a PXRD pattern (CuKα λ=1.5418 Å at a temperature of about 25° C.) comprising four or more, preferably five or more, 2θ values selected from: 7.4±0.2; 10.4±0.2; 12.2±0.2; 13.4±0.2; 18.9±0.2; 19.7±0.2; 21.5±0.2; and 22.0±0.2, wherein the PXRD pattern of Form H1.5-2 is measured at a temperature of about 25° C.

In yet an even further embodiment, the H1.5-2 Form is characterized by fractional atomic coordinates substantially as listed in Table 3.

TABLE 3

Fractional Atomic Coordinates of Form H1.5-2 Calculated
at a Temperature of About −30° C.

| Atom | X | Y | Z |
|---|---|---|---|
| Cl1 | −0.15270 | 0.49160 | 0.18137 |
| N1 | 0.58664 | 0.23703 | 0.82434 |
| N3 | −0.37307 | 0.45557 | 0.53029 |
| N2 | 0.27223 | 0.28648 | 0.64683 |
| N4 | −0.39084 | 0.51293 | 0.33149 |

TABLE 3-continued

Fractional Atomic Coordinates of Form H1.5-2 Calculated at a Temperature of About −30° C.

| Atom | X | Y | Z |
|---|---|---|---|
| O2 | 0.30852 | 0.21290 | 0.49147 |
| O1 | 0.33415 | 0.13073 | 0.70485 |
| O3 | 0.50845 | 0.30848 | 0.70078 |
| O4 | −0.03845 | 0.41635 | 0.36481 |
| F1 | 0.94787 | 0.37296 | 0.95668 |
| F2 | 0.02760 | 0.31544 | 0.25765 |
| C13 | 0.41698 | 0.21956 | 0.69982 |
| C9 | 0.19044 | 0.31698 | 0.57502 |
| C12 | 0.32845 | 0.23890 | 0.60171 |
| C5 | −0.31024 | 0.41965 | 0.60150 |
| C15 | 0.50259 | 0.14636 | 0.83660 |
| C7 | 0.06805 | 0.33227 | 0.38498 |
| C14 | 0.41730 | 0.16446 | 0.74691 |
| C2 | −0.21148 | 0.46367 | 0.34715 |
| C8 | 0.14531 | 0.29840 | 0.44814 |
| C6 | 0.03273 | 0.38285 | 0.44330 |
| C17 | 0.50228 | 0.25873 | 0.73879 |
| C3 | −0.14860 | 0.42722 | 0.42517 |
| C1 | −0.32469 | 0.47774 | 0.40294 |
| C4 | −0.19901 | 0.40406 | 0.55560 |
| C18 | 0.68036 | 0.27306 | 0.85950 |
| C16 | 0.58344 | 0.18281 | 0.87120 |
| C10 | 0.15491 | 0.36835 | 0.63630 |
| C23 | 0.65843 | 0.31982 | 0.94681 |
| C11 | 0.07647 | 0.40081 | 0.57030 |
| C21 | 0.85918 | 0.33968 | 0.92510 |
| C19 | 0.79203 | 0.26014 | 0.80450 |
| C20 | 0.88262 | 0.29394 | 0.83870 |
| C22 | 0.74870 | 0.35362 | 0.98040 |
| C24 | 0.32599 | 0.07346 | 0.75740 |
| C25 | 0.23329 | 0.04566 | 0.68070 |
| O99 | 0.38858 | 0.39284 | 0.86939 |
| O98 | 0.55213 | 0.46703 | 1.00819 |
| H2 | 0.28869 | 0.29978 | 0.73020 |
| H4A | −0.46033 | 0.52017 | 0.36771 |
| H4B | −0.36353 | 0.52807 | 0.24961 |
| H5 | −0.34442 | 0.40398 | 0.68870 |
| H15 | 0.50269 | 0.10970 | 0.87130 |
| H8 | 0.16678 | 0.26389 | 0.40680 |
| H4 | −0.15892 | 0.37888 | 0.60980 |
| H16 | 0.63979 | 0.17059 | 0.92970 |
| H10 | 0.18428 | 0.38078 | 0.72210 |
| H23 | 0.58289 | 0.32858 | 0.98300 |
| H11 | 0.05298 | 0.43508 | 0.61180 |
| H19 | 0.80649 | 0.22879 | 0.74460 |
| H20 | 0.95829 | 0.28539 | 0.80290 |
| H22 | 0.73500 | 0.38518 | 1.03930 |
| H24A | 0.30659 | 0.07270 | 0.86360 |
| H24B | 0.39919 | 0.05430 | 0.73470 |
| H25A | 0.16338 | 0.06720 | 0.69580 |
| H25B | 0.21969 | 0.00870 | 0.72030 |
| H25C | 0.25718 | 0.04320 | 0.57691 |
| H99A | 0.43402 | 0.37403 | 0.81899 |
| H99B | 0.35202 | 0.36703 | 0.94500 |
| H98B | 0.52551 | 0.50247 | 1.00958 |
| H98A | 0.50251 | 0.44452 | 0.96608 |

Figure 7:
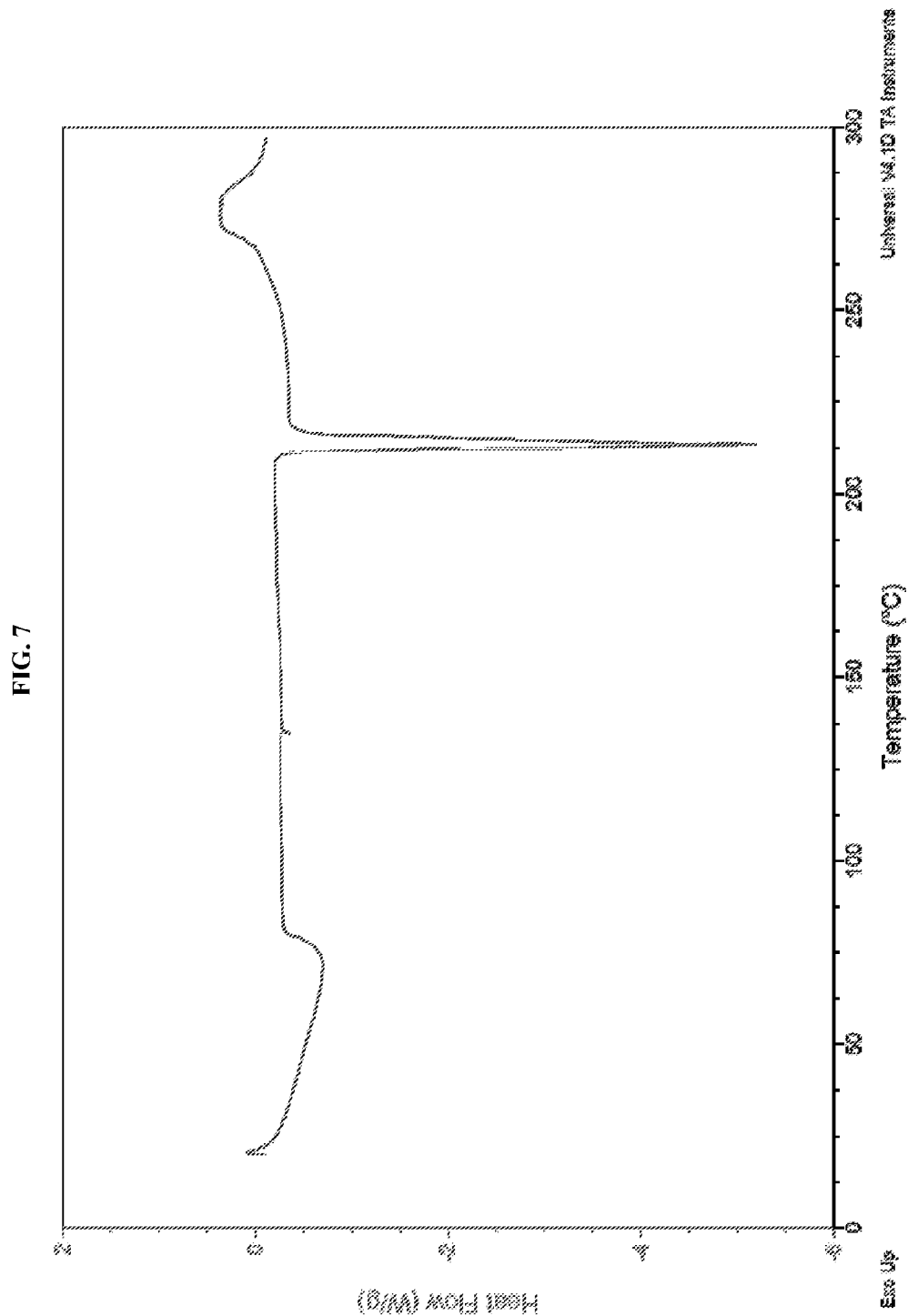
FIG. 7 shows a DSC thermogram of the H1.5-2 Form of Compound (I).

In a still further embodiment, the H1.5-2 Form is characterized by a differential scanning calorimetry (DSC) thermogram substantially in accordance with that shown in FIG. 7.

In still yet a further embodiment, the H1.5-2 Form is characterized by a thermogravimetric analysis (TGA) thermogram having weight loss in the range of from about 2 to about 5 wt. %, based on the weight of the sample of Form H1.5-2, upon being heated to a temperature of about 150° C.

Figure 12:
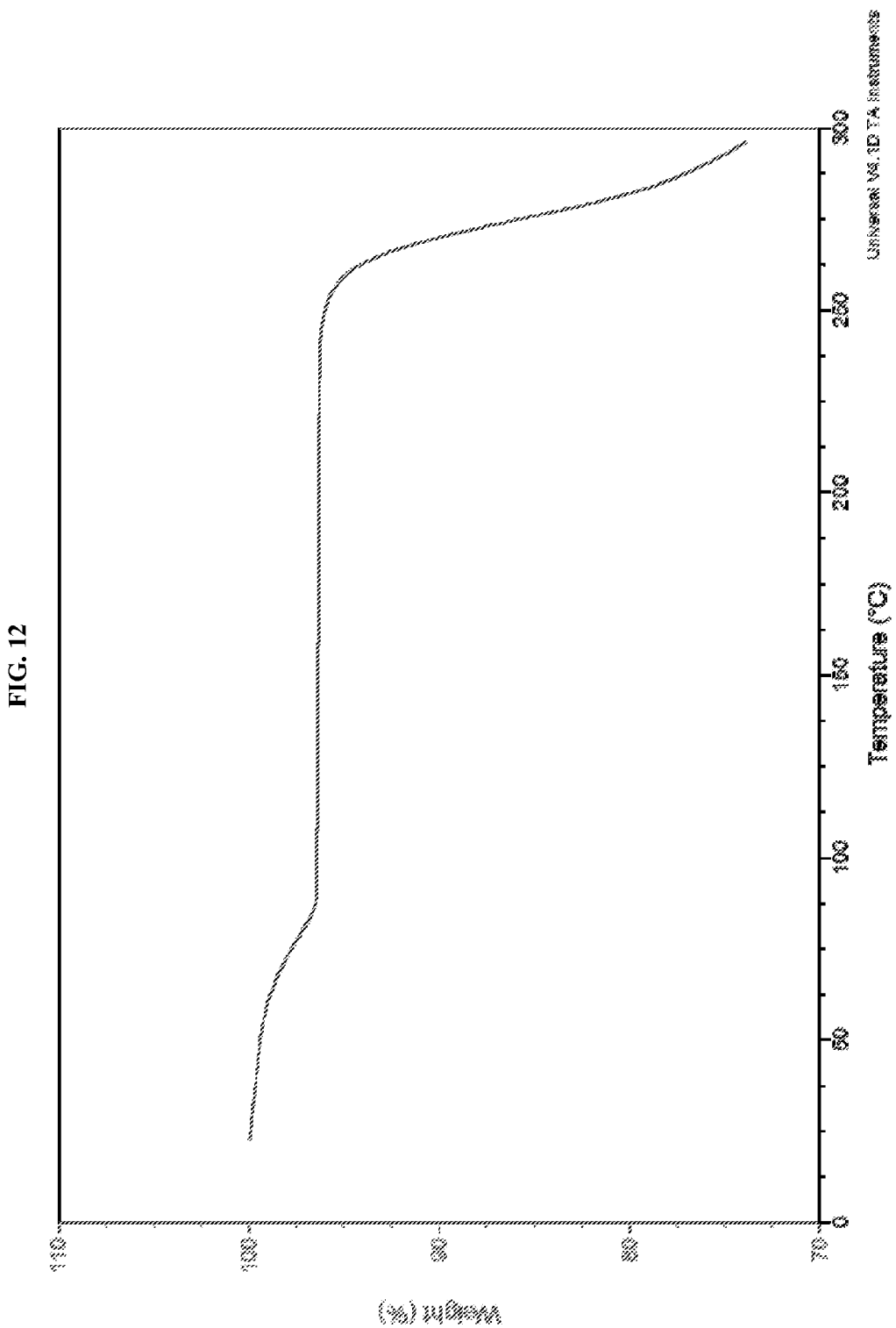
FIG. 12 shows a TGA thermogram of the H1.5-2 Form of Compound (I).

In still another embodiment, the H1.5-2 Form exhibits a TGA thermogram substantially the same as shown in FIG. 12.

In still yet an even further embodiment, the second crystalline form of Compound (I) is substantially pure.

In still yet another embodiment, the second crystalline form of Compound (I) contains at least about 90 wt. %, preferably at least about 95 wt. %, and more preferably at least about 99 wt. %, based on weight of the second crystalline form, Form H1.5-2.

In yet another embodiment, a substantially pure second crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form has substantially pure phase homogeneity with less than about 1% of the total peak area of the experimentally measured PXRD pattern arising from peaks that are absent from the simulated PXRD pattern.

In another embodiment, the second crystalline form of Compound (I) consists essentially of Form H1.5-2. The second crystalline form of this embodiment may comprise at least about 90 wt. %, preferably at least about 95 wt. %, and more preferably at least about 99 wt. %, based on the weight of the second crystalline form, Form H1.5-2.

In yet another embodiment, a pharmaceutical composition comprises Form H1.5-2; and at least one pharmaceutically-acceptable carrier and/or diluent.

In still another embodiment, a pharmaceutical composition comprises substantially pure Form H1.5-2; and at least one pharmaceutically-acceptable carrier and/or diluent.

In still an even further embodiment, a therapeutically effective amount of Form H1.5-2 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of Compound (I), wherein Compound (I) is provided in a second crystalline form comprising Form H1.5-2. Preferably, the patient is a human. The method of this embodiment can be used to treat proliferative diseases selected from bladder cancer, breast cancer, colorectal cancer, gastric cancer, head and neck cancer, kidney cancer, liver cancer, lung cancer, ovarian cancer, pancreas/gallbladder cancer, prostate cancer, thyroid cancer, osteosarcoma, rhabdomyosarcoma, glioblastomas/astrocytomas, melanoma, MFH/fibrosarcoma, and mesothelioma; and preferably, lung cancer, head and neck cancer, gastric cancer, or bladder cancer.

In an even further embodiment, the method comprises administering Compound (I), wherein Compound (I) consisting essentially of Form H1.5.2.

Form H-1

A first crystalline form of a mono-hydrochloric acid salt of Compound (I) comprises a monohydrate crystalline form referred to herein as "Form H-1" or "H-1 Form". The monohydrate crystalline form of the mono-hydrochloric acid salt of Compound (I) comprises one mole of HCl and up to one mole of water for each mole of Compound (I).

In one embodiment, the H-1 Form is characterized by unit cell parameters approximately equal to the following:
Cell dimensions:
a=14.45 Å
b=25.34 Å
c=7.09 Å
α=90.0°
β=100.2°
γ=90.0°
Space group: P2$_1$/c
Molecules of Compound (I)/asymmetric unit: 1
Volume=638 Å$^3$
Density (calculated)=1.476 g/cm$^3$, wherein the unit cell parameters of Form H-1 are measured at a temperature of about 25° C.

In one embodiment, the H-1 Form is characterized by unit cell parameters approximately equal to the following:
Cell dimensions:
a=14.42 Å
b=25.38 Å
c=7.02 Å
α=90.0°
β=100.1°
γ=90.0°
Space group: P2₁/c
Molecules of Compound (I)/asymmetric unit: 1
Volume=632 Å³
Density (calculated)=1.443 g/cm³,
wherein the unit cell parameters of Form H-1 are measured at a temperature of about −50° C.

Figure 3:
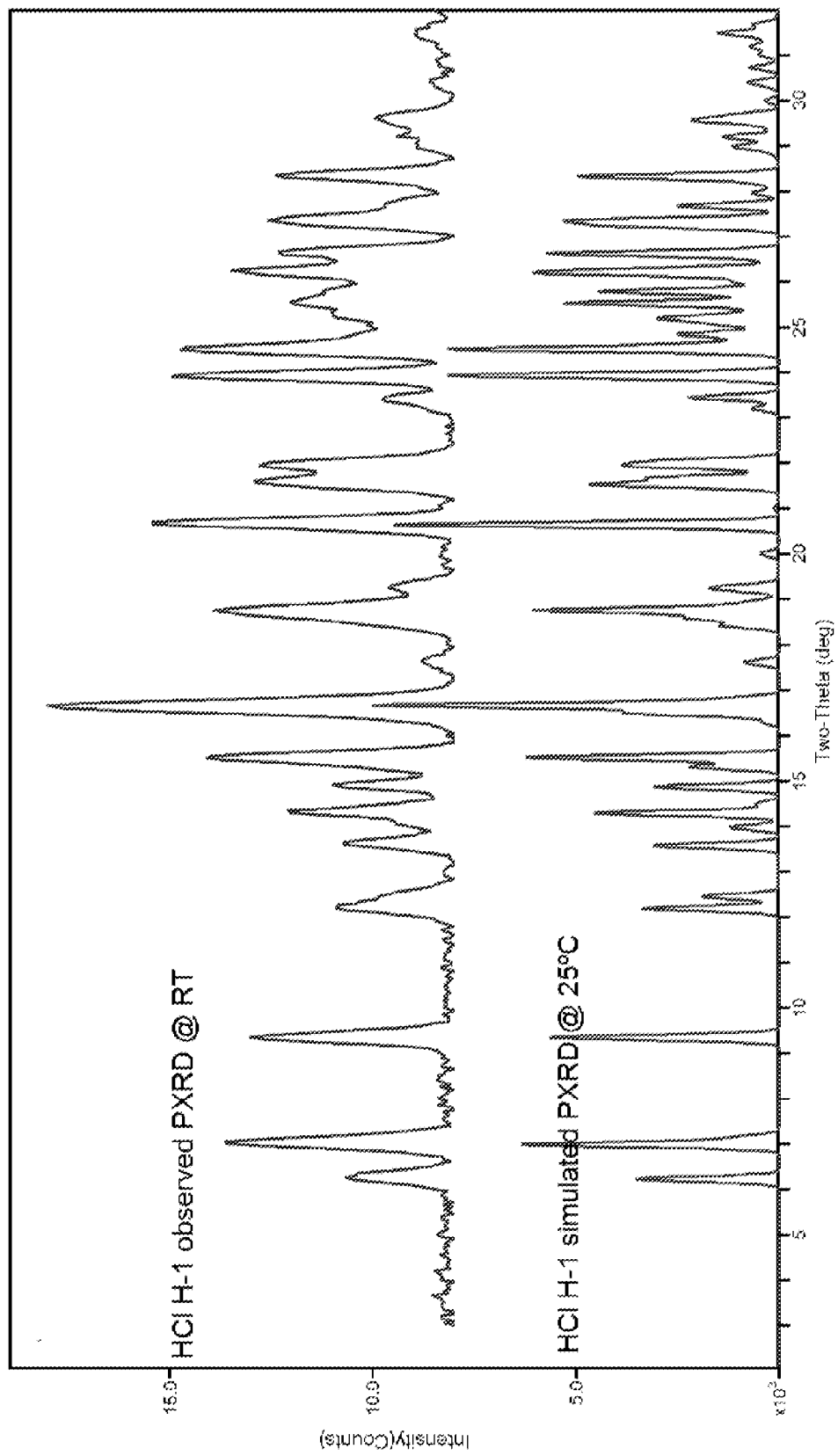
FIG. 3 shows observed (at r.t.) and simulated (at about 25° C.) PXRD patterns (CuKα λ=1.5418 Å) of the H-1 Form of the mono-hydrochloric acid salt of Compound (I).

In another embodiment, the H-1 Form is characterized by a simulated PXRD pattern substantially in accordance with the pattern shown in FIG. 3 and/or by a simulated PXRD pattern substantially in accordance with the pattern shown in FIG. 3.

In yet another embodiment, the H-1 Form is characterized by a PXRD pattern (CuKα λ=1.5418 Å at a temperature of about 25° C.) comprising four or more, preferably five or more, 2θ values (CuKα λ=1.5418 Å) selected from: 6.3±0.2, 7.0±0.2, 9.4±0.2, 15.5±0.2, 16.6±0.2, 18.7±0.2, 20.7±0.2, and 23.9±0.2, wherein the PXRD pattern of Form H-1 is measured at a temperature of about 25° C.

In yet an even further embodiment, the H-1 Form is characterized by fractional atomic coordinates substantially as listed in Table 4.

TABLE 4

Fractional Atomic Coordinates of Form H-1
Calculated at a Temperature of about 25° C.

| Atom | X | Y | Z |
|---|---|---|---|
| Cl1 | −0.10459 | 0.41343 | 0.62667 |
| N3 | 0.37675 | 0.22314 | 0.90670 |
| O4 | 0.05914 | 0.35180 | 0.77450 |
| O5 | 0.45787 | 0.09702 | 1.13041 |
| C6 | 0.38211 | 0.17158 | 0.86900 |
| O7 | 0.51487 | 0.21016 | 0.64480 |
| C8 | 0.47931 | 0.14990 | 0.87721 |
| C9 | 0.29461 | 0.25442 | 0.88071 |
| N10 | 0.61872 | 0.14295 | 0.73660 |
| O11 | 0.31320 | 0.14282 | 0.82320 |
| C12 | 0.53501 | 0.17077 | 0.74670 |
| C13 | 0.20643 | 0.23405 | 0.88601 |
| F14 | 0.04506 | 0.24828 | 0.86530 |
| C15 | 0.03243 | 0.38165 | 0.91201 |
| N16 | −0.03366 | 0.44318 | 1.17040 |
| C17 | 0.51091 | 0.10881 | 0.99821 |
| C18 | 0.07963 | 0.38291 | 1.10081 |
| C19 | 0.22702 | 0.34047 | 0.81431 |
| C20 | 0.14023 | 0.32018 | 0.82020 |
| C21 | 0.13072 | 0.26747 | 0.85690 |
| C22 | 0.30532 | 0.30808 | 0.84630 |
| C23 | 0.67990 | 0.16142 | 0.61250 |
| C24 | −0.07986 | 0.44412 | 0.99000 |
| C26 | −0.04576 | 0.41229 | 0.85730 |
| C27 | 0.64381 | 0.09986 | 0.85041 |
| C28 | 0.04403 | 0.41420 | 1.22591 |
| C29 | 0.64500 | 0.17169 | 0.41940 |
| N30 | −0.15746 | 0.47454 | 0.94800 |
| C31 | 0.59531 | 0.08259 | 0.97991 |
| C32 | 0.77370 | 0.16929 | 0.68380 |
| C33 | 0.48452 | 0.05383 | 1.26231 |
| C34 | 0.83389 | 0.18526 | 0.56200 |
| C35 | 0.79749 | 0.19391 | 0.37370 |
| F36 | 0.85769 | 0.20853 | 0.25650 |

TABLE 4-continued

Fractional Atomic Coordinates of Form H-1
Calculated at a Temperature of about 25° C.

| Atom | X | Y | Z |
|---|---|---|---|
| C37 | 0.70529 | 0.18809 | 0.30150 |
| C38 | 0.41882 | 0.05389 | 1.39750 |
| O25 | −0.29402 | 0.52778 | 1.65579 |
| Cl2 | −0.16061 | 0.52246 | 1.34879 |
| H29 | 0.57922 | 0.16708 | 0.36977 |
| H37 | 0.68087 | 0.19543 | 0.16917 |
| H34 | 0.89952 | 0.19110 | 0.61010 |
| H32 | 0.79718 | 0.16312 | 0.81738 |
| H27 | 0.69936 | 0.08032 | 0.83787 |
| H31 | 0.61596 | 0.05286 | 1.06034 |
| C38 | 0.41882 | 0.05389 | 1.39750 |
| O25 | −0.29402 | 0.52778 | 1.65579 |
| Cl2 | −0.16061 | 0.52246 | 1.34879 |
| H29 | 0.57922 | 0.16708 | 0.36977 |
| H37 | 0.68087 | 0.19543 | 0.16917 |
| H34 | 0.89952 | 0.19110 | 0.61010 |
| H32 | 0.79718 | 0.16312 | 0.81738 |
| H27 | 0.69936 | 0.08032 | 0.83787 |
| H31 | 0.61596 | 0.05286 | 1.06034 |
| — | — | — | — |

Figure 8:
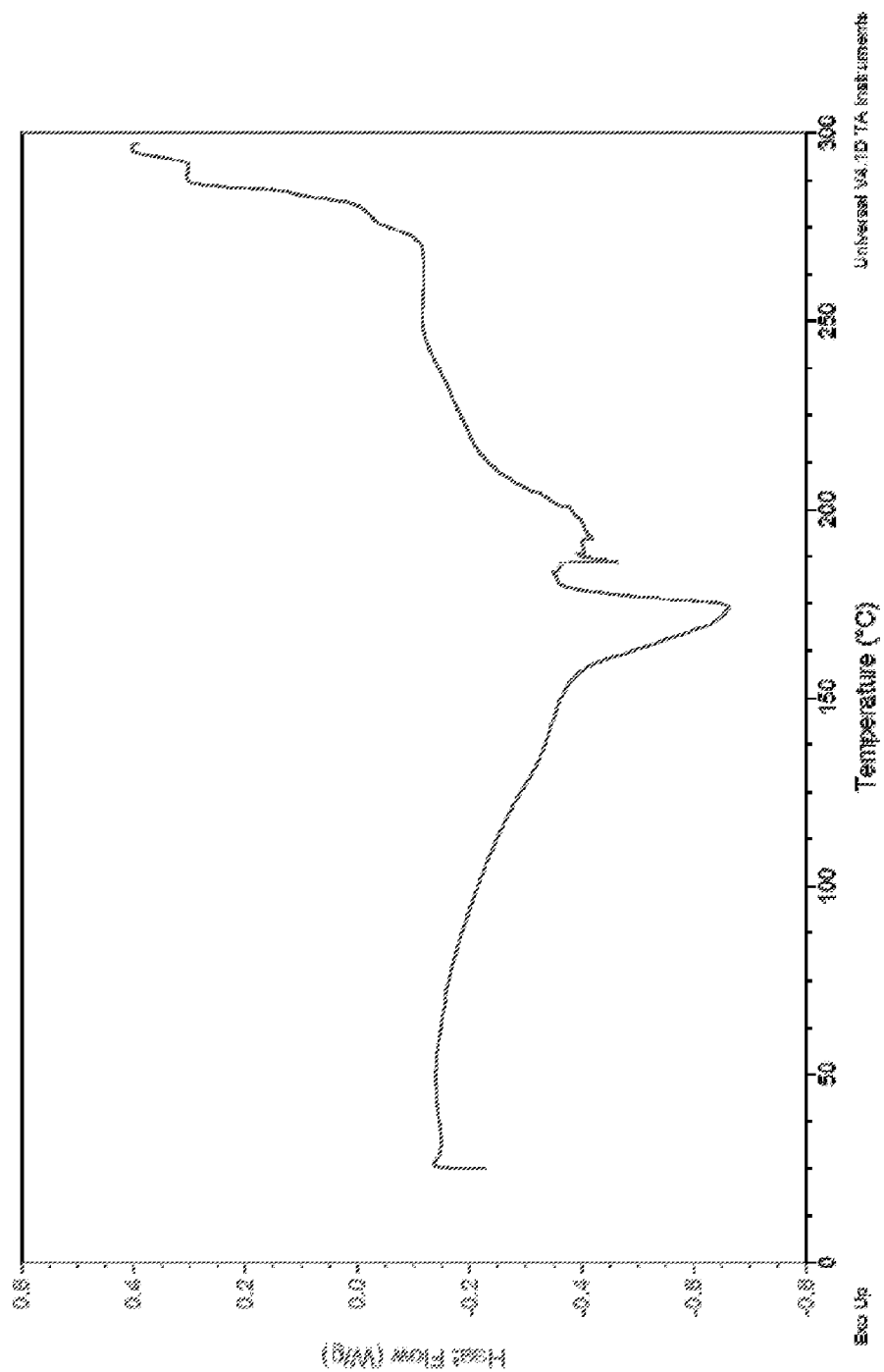
FIG. 8 shows a DSC thermogram of the H-1 Form of the hydrochloric acid salt of Compound (I).

In a still further embodiment, the H-1 Form is characterized by a DSC thermogram substantially in accordance with that shown in FIG. 8.

Figure 13:
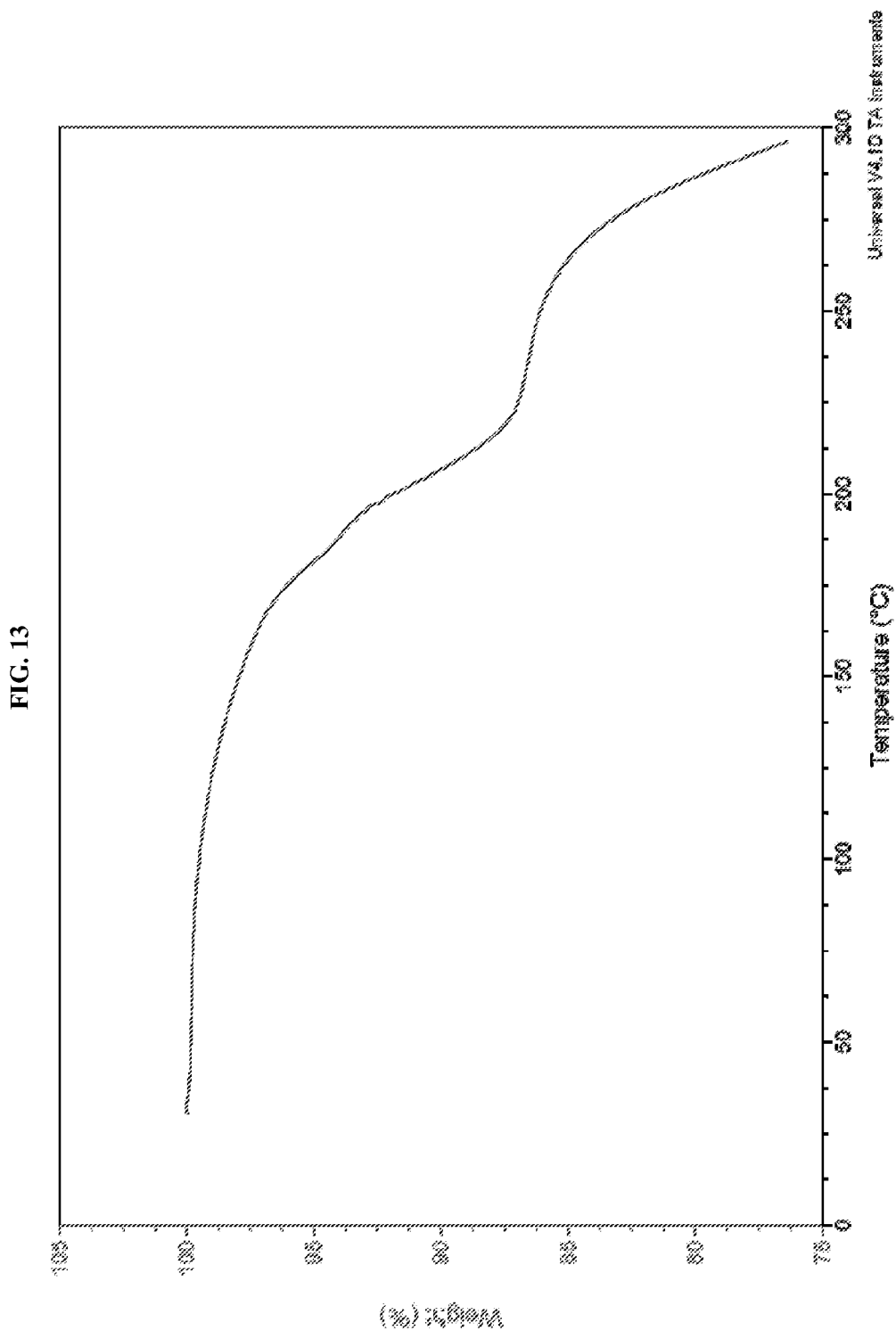
FIG. 13 shows a TGA thermogram of the H-1 Form of the hydrochloric acid salt of Compound (I).

In still another embodiment, the H-1 Form exhibits a TGA thermogram substantially the same as shown in FIG. 13.

In still yet an even further embodiment, the H-1 Form of Compound (I) is substantially pure.

Form N-2

A second crystalline form of mono-hydrochloric acid salt of Compound (I) comprises a neat crystalline form referred to herein as "Form N-2" or "N-2 Form". The second crystalline form of the mono-hydrochloric acid salt of Compound (I) comprises one mole of HCl for each mole of Compound (I).

Figure 4:
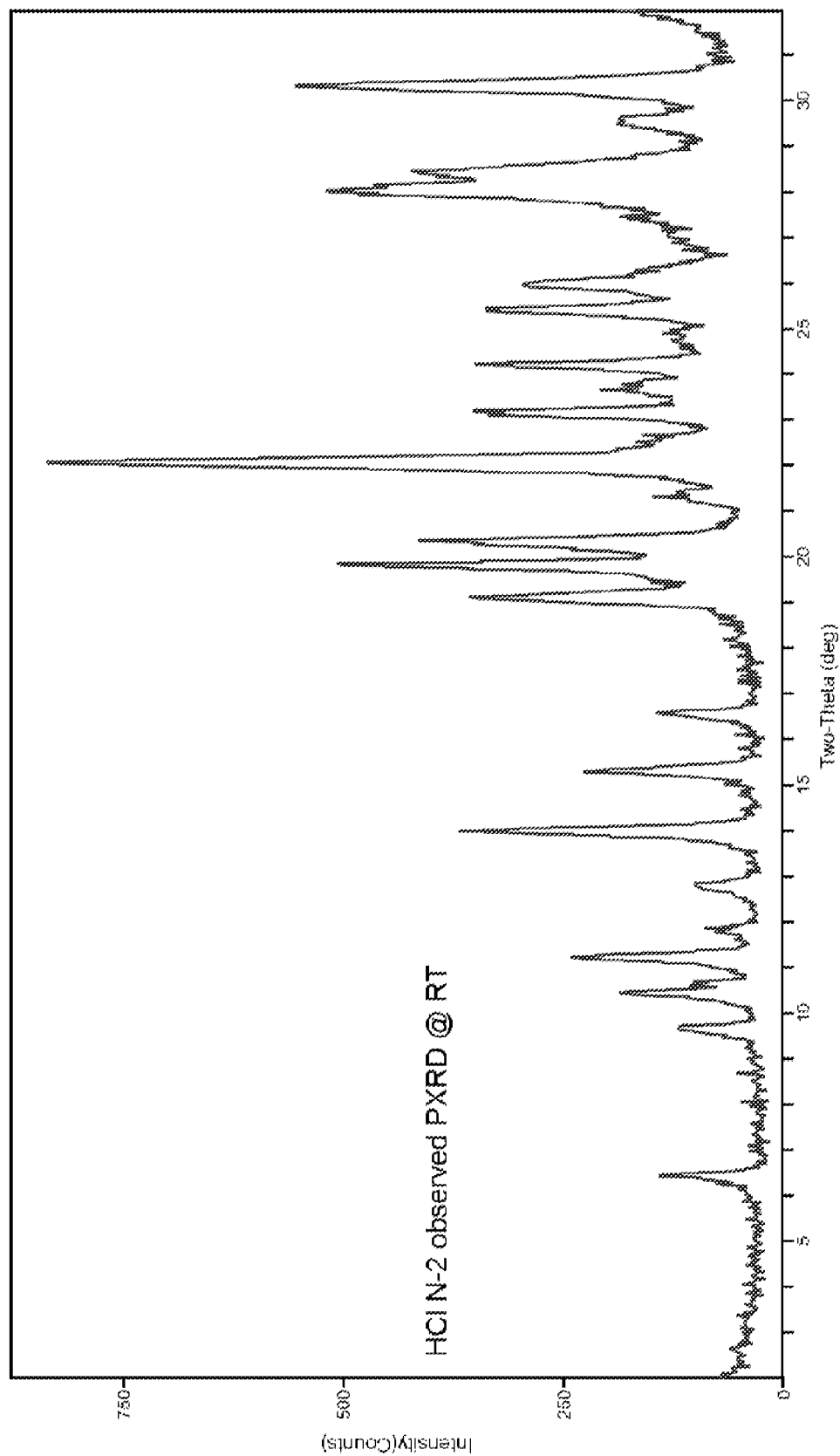
FIG. 4 shows observed (at r.t.) PXRD pattern (CuKα λ=1.5418 Å) of the N-2 Form of the mono-hydrochloric acid salt of Compound (I).

In another embodiment, the N-2 Form is characterized by a simulated PXRD pattern substantially in accordance with the pattern shown in FIG. 4 and/or by a simulated PXRD pattern substantially in accordance with the pattern shown in FIG. 4.

In yet another embodiment, the N-2 Form is characterized by a PXRD pattern (CuKα λ=1.5418 Å at a temperature of about 25° C.) comprising four or more, preferably five or more, 2θ values (CuKα λ=1.5418 Å) selected from: 6.4±0.2, 9.6±0.2, 10.4±0.2, 11.2±0.2, 14.0±0.2, 15.2±0.2, 16.5±0.2, 19.1±0.2, and 22.0±0.2, wherein the PXRD pattern of Form N-2 is measured at a temperature of about 25° C.

Figure 9:
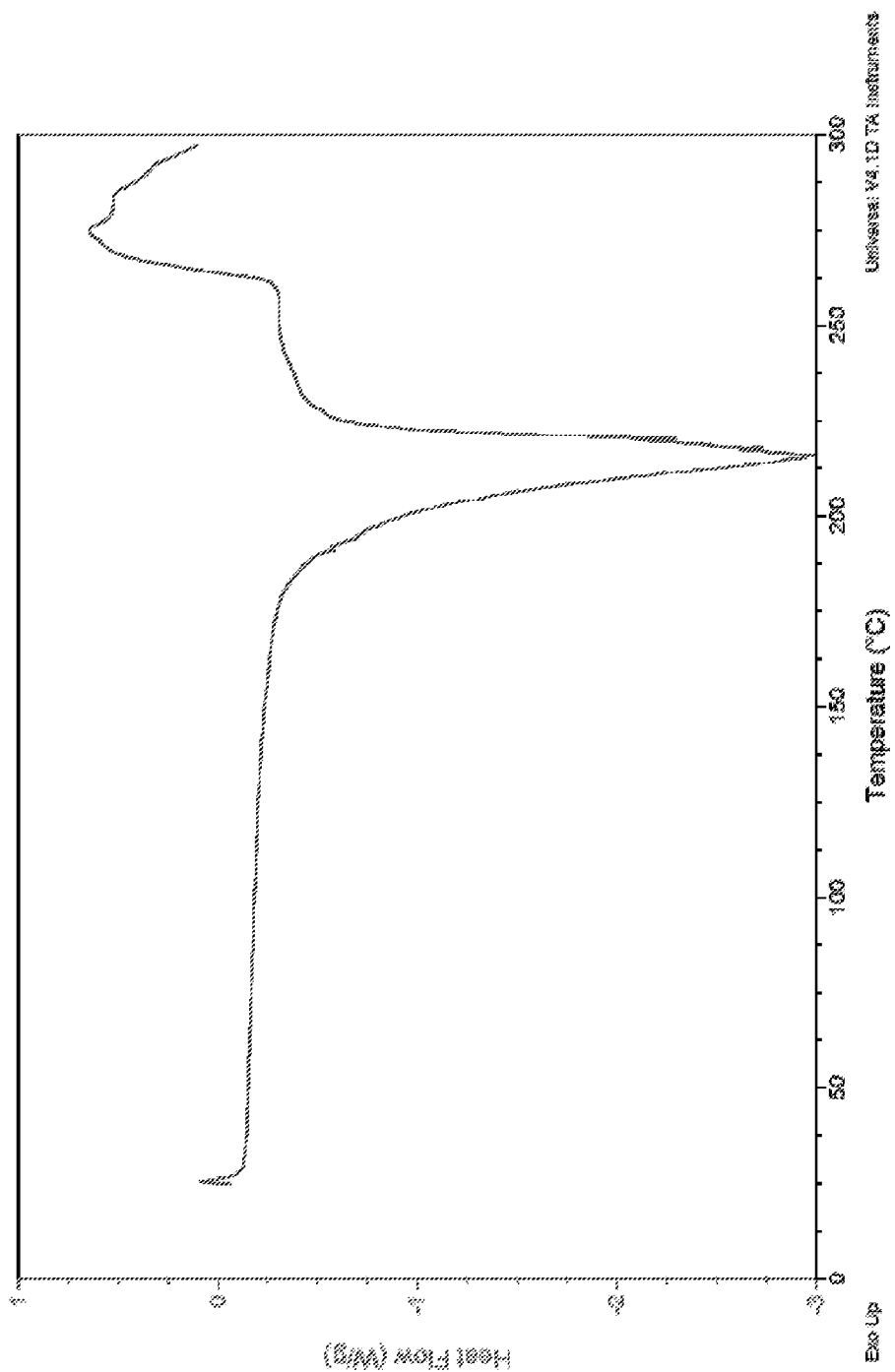
FIG. 9 shows a DSC thermogram of the N-2 Form of the hydrochloric acid salt of Compound (I).

In a still further embodiment, the N-2 Form is characterized by a DSC thermogram substantially in accordance with that shown in FIG. 9.

Figure 14:
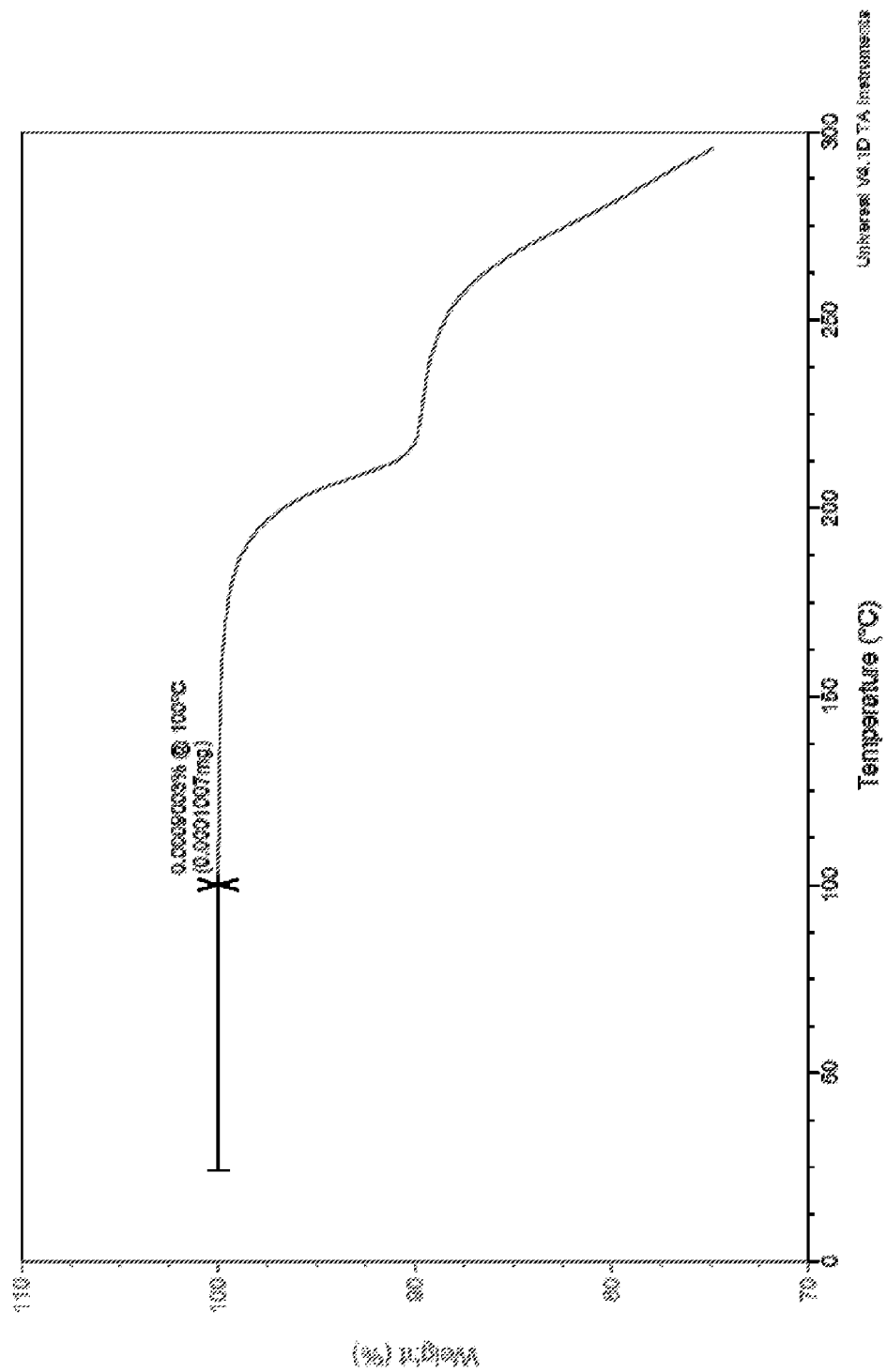
FIG. 14 shows a TGA thermogram of the N-2 Form of the hydrochloric acid salt of Compound (I).

In still another embodiment, the N-2 Form exhibits a TGA thermogram substantially the same as shown in FIG. 14.

Figure 17:
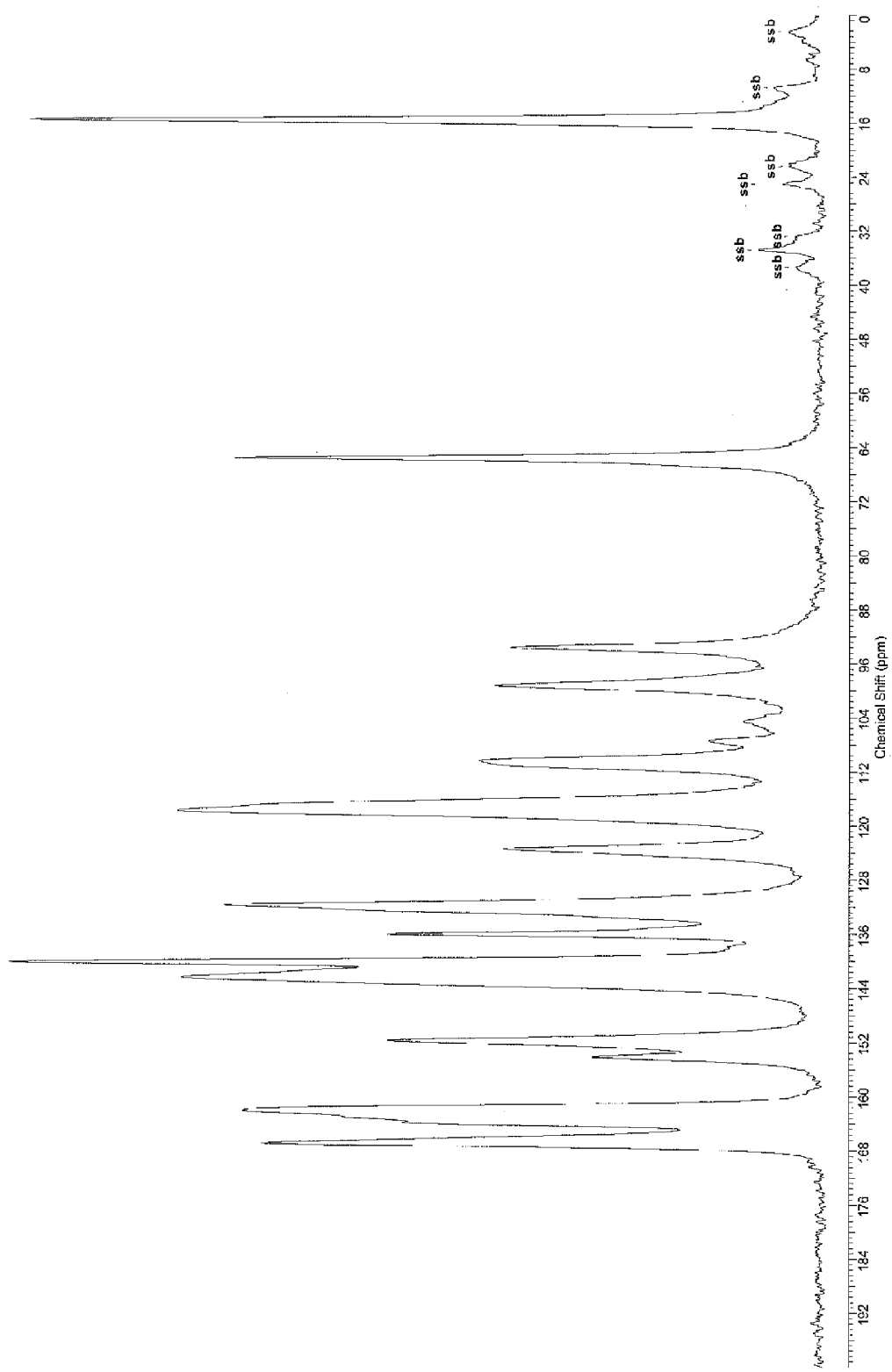
FIG. 17 shows the ssNMR of the N-2 Form of a HCl salt of Compound (I).

In another embodiment, the N-2 Form is characterized by a solid state nuclear magnetic resonance spectra (ssNMR) substantially in accordance with the spectra shown in FIG. 17.

In still yet an even further embodiment, the N-2 crystalline form of Compound (I) is substantially pure.

In still yet another embodiment, the second crystalline form of the mono-hydrochloric acid salt of Compound (I) contains at least about 90 wt. %, preferably at least about 95 wt. %, and more preferably at least about 99 wt. %, based on the weight of Form N-2.

In yet another embodiment, a substantially pure second crystalline form of the mono-hydrochloric acid salt of Compound (I) has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form of the mono-hydrochloric acid salt of Compound (I) has substantially pure phase homogeneity with less than about 1% of the total peak area of the experimentally measured PXRD pattern arising from peaks that are absent from the simulated PXRD pattern.

Phosphoric Acid Salt

A phosphoric acid salt of Compound (I) is provided comprising one mole of phosphoric acid for each mole of Compound (I). The phosphoric acid salt of Compound (I) can be amorphous, crystalline, or mixtures thereof.

Figure 5:
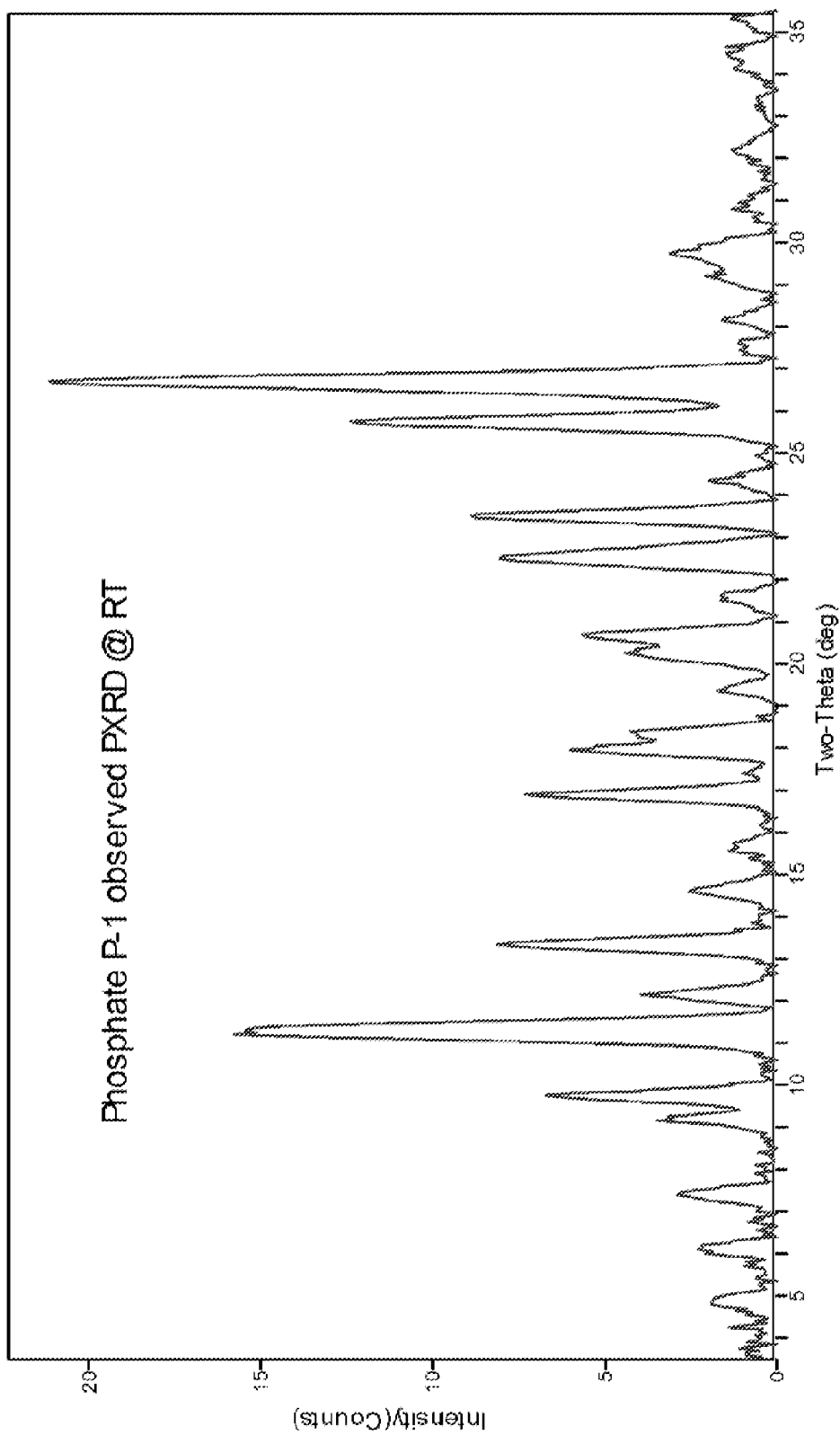
FIG. 5 shows observed (at r.t.) PXRD pattern (CuKα λ=1.5418 Å) of the phosphoric acid salt of Compound (I).

In one embodiment, the phosphoric acid salt of Compound (I) is characterized by an observed PXRD pattern substantially in accordance with the pattern shown in FIG. 5.

In yet another embodiment, the phosphoric acid salt of Compound (I) is characterized by a PXRD pattern (CuK$\alpha$ $\lambda$=1.5418 Å at a temperature of about 25° C.) comprising four or more, preferably five or more, 2θ values (CuK$\alpha$ $\lambda$=1.5418 Å) selected from: 4.8±0.2, 6.1±0.2, 7.4±0.2, 9.2±0.2, 9.7±0.2, 11.3±0.2, 12.2±0.2, 13.3±0.2, 16.9±0.2, 22.5±0.2, and 23.5±0.2, wherein the PXRD pattern of the salt is measured at a temperature of about 25° C.

Figure 10:
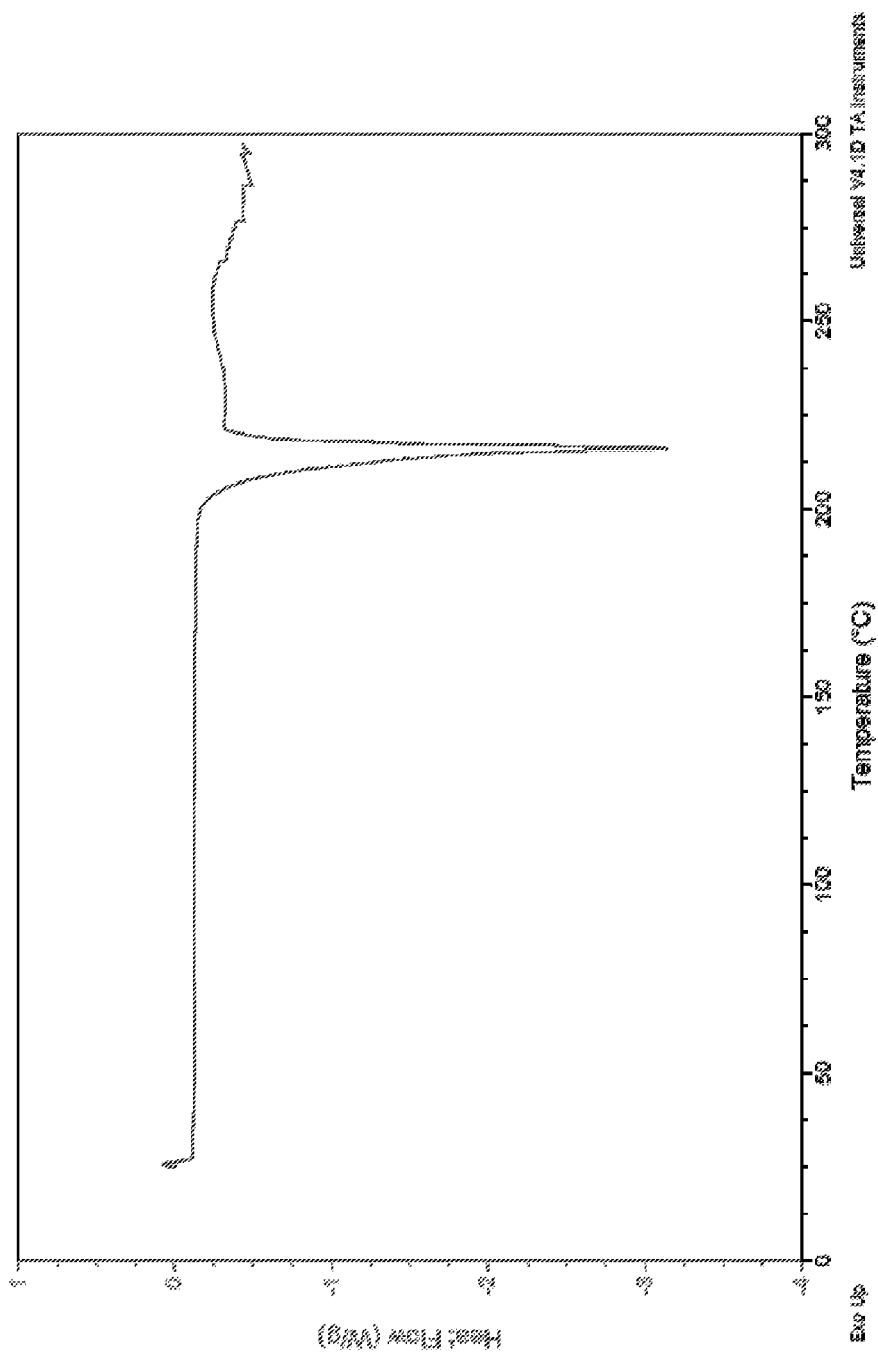
FIG. 10 shows a DSC thermogram of the phosphoric acid salt of Compound (I).

In a still further embodiment, the phosphoric acid salt of Compound (I) is characterized by a DSC thermogram substantially in accordance with that shown in FIG. 10.

Figure 15:
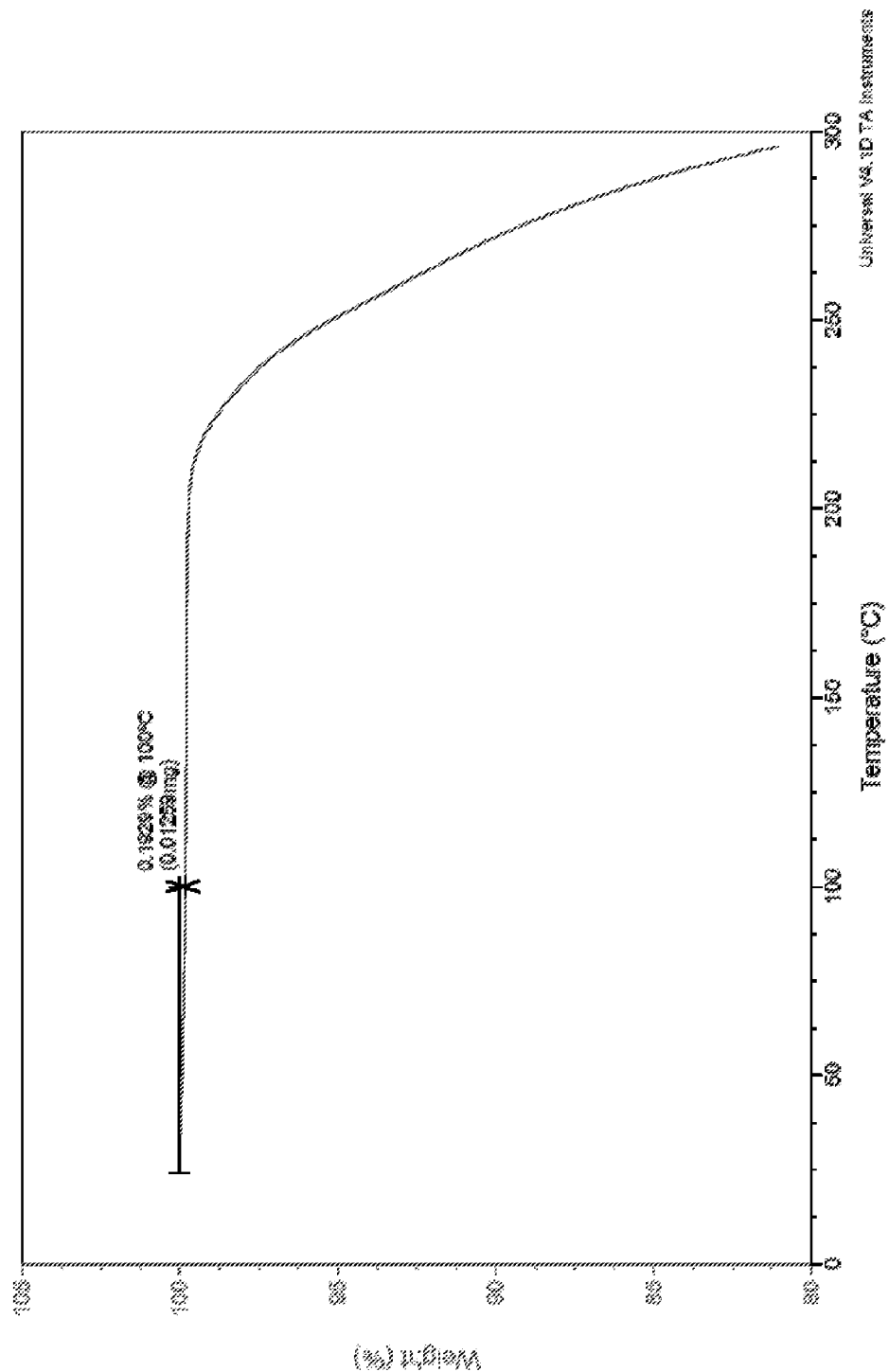
FIG. 15 shows a TGA thermogram of the phosphoric acid salt of Compound (I).

In still another embodiment, the phosphoric acid salt of Compound (I) exhibits a TGA thermogram substantially the same as shown in FIG. 15.

Form N-1 is surprisingly advantageous because it has a combination of properties that make it suitable for pharmaceutical drug production and administration of Compound (I) to a patient. Form N-1 has suitable chemical and physical stability, such as stability of the form during processing to the desired dosage form and/or stability during storage. Form N-1 shows suitable chemical and physical stability as indicated by testing at several different temperature and humidity conditions.

Compound (I) may be administered by any suitable route, preferably in the form of a pharmaceutical composition adapted to such a route, and in a dose effective for the treatment intended. For example, compound (I) may be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

In one embodiment, a pharmaceutical composition is provided comprising crystalline Form N-1 of Compound (I) and at least one pharmaceutically acceptable carrier and/or diluent. Preferably, the pharmaceutical composition comprises a therapeutically acceptable amount of Form N-1 of Compound (I).

Pharmaceutically acceptable carriers, diluents, adjuvants and vehicles that may be used in the pharmaceutical compositions of this invention include, but are not limited to, ion exchangers, alumina, aluminum stearate, lecithin, self-emulsifying drug delivery systems (SEDDS) such as D-a-tocopherol polyethyleneglycol 1000 succinate, surfactants used in pharmaceutical dosage forms such as TWEEN surfactants (ICI Americas, Inc., Delaware) or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrins, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Any pharmaceutical composition contemplated herein can, for example, be delivered orally via any acceptable and suitable oral preparations. Exemplary oral preparations, include, but are not limited to, for example, tablets; troches; lozenges; aqueous or oily suspensions; dispersible powders or granules; emulsions; hard or soft capsules; syrups; and elixirs. Pharmaceutical compositions intended for oral administration can be prepared according to methods known in the art and can contain at least one agent selected from sweetening agents, flavoring agents, coloring agents, demulcents, antioxidants, and preserving agents.

Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc.

Oily suspensions can, for example, be prepared by suspending Form N-1 of Compound (I) in either a vegetable oil, such as, for example, arachis oil; olive oil; sesame oil; and coconut oil; or in mineral oil, such as, for example, liquid paraffin.

A pharmaceutical composition contemplated herein can, for example, also be delivered intravenously, subcutaneously, and/or intramuscularly via any pharmaceutically acceptable and suitable injectable composition. Form N-1 can be dissolved and/or dispersed into a sterile aqueous solutions comprising acceptable vehicles and solvents, such as, for example, water, Ringer's solution, and isotonic sodium chloride solution; sterile oil-in-water microemulsions; and aqueous or oleaginous suspensions to provide an injectable composition.

A sterile injectable oil-in-water microemulsion can, for example, be prepared by 1) dissolving Form N-1 of Compound (I) in an oily phase, such as, for example, a mixture of soybean oil and lecithin; 2) combining the Compound (I) containing oil phase with a water and glycerol mixture; and 3) processing the combination to form a microemulsion.

Any pharmaceutical composition contemplated herein can, for example, further be administered via any acceptable and suitable rectal preparation, including, but not limited to, for example, a suppository. A suppository can be prepared by mixing Form N-1 of Compound (I) with at least one suitable non-irritating excipient that is liquid at rectal temperatures but solid at a temperature below rectal temperature.

Any pharmaceutical composition contemplated herein can, for example, be administered via any acceptable and suitable topical preparations including, but not limited to, for example, creams; ointments; jellies; solutions; suspensions, transdermal patches; and intranasal inhalers. For purposes of this application, topical preparations include mouth washes and gargles.

For oral administration, the pharmaceutical composition may be in the form of, for example, a tablet, capsule, suspension or liquid. Tablets and pills can additionally be prepared with barrier membranes or enteric coatings such as, for example, ethyl cellulose and methacrylic acid polymer. Such compositions may also comprise adjuvants, such as wetting, sweetening, flavoring, and perfuming agents. Form N-1 of Compound (I) may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may additionally contain swellable polymer such as hydroxypropyl methyl cellulose, hydroxypropyl cellulose, and povidone to provide sustained release formulations.

The pharmaceutical composition is preferably made in the form of a dosage unit containing a particular amount of the active ingredient. Examples of such dosage units were tablets or capsules. For example, these may contain an amount of Compound (I) from about 1 to 200 mg, preferably from about 1 to 150 mg, more preferably from about 5 to 100 mg. A suitable daily dose for a human or other mammal may vary widely depending on the condition of the patient and other factors, but, once again, can be determined using routine methods.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, Form N-1 may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

Compound (I) can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include TWEEN 60 surfactant, SPAN 80 surfactant (ICI Americas Inc., Delaware), cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. Form N-1 of Compound (I) may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., TWEEN 80 surfactant).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical composition of this invention can be prepared in accordance with conventional methods of pharmacy. The pharmaceutical composition may be subjected to conventional pharmaceutical operations such as sterilization and/or may contain conventional adjuvants, such as preservatives, stabilizers, wetting agents, emulsifiers, buffers etc.

Pharmaceutical compositions of this invention comprising Compound (I); and optionally an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc), immunosuppressants, anti-cancer agents, anti-viral agents, antiinflammatory agents, antifungal agents, antibiotics, or anti-vascular hyperproliferation compounds.

Pharmaceutical Compositions Comprising Form N-1 of Compound (I)

Pharmaceutical compositions are provided comprising (i) particles of Compound (I) in Form N-1; (ii) a stabilizer; and (iii) at least one pharmaceutically acceptable carrier and/or diluent; wherein said particles have a diameter ($D_{90}$) in the range of from 1 to 50 microns and said stabilizer is disposed on said particles. The term "disposed" is used herein to indicate that the stabilizer has sufficient contact with the Form N-1 particles of Compound (I) to minimize or prevent conversion of the Form N-1 particles to another form, including conversion to the sesquihydrate Form H1.5-1 upon exposure to moisture or water. The stabilizer may provide partial or complete coverage of the surfaces of the particles, or alternatively may be partially or completely adsorbed onto the particle surfaces and/or into the particles.

Microsuspension Pharmaceutical Compositions Comprising Form N-1 of Compound (I)

The neat N-1 Form of Compound (I) has an aqueous solubility of about 0.25 μg/ml at pH 7.4 and room temperature. However, in the presence of an aqueous medium, the neat crystalline Form N-1 can convert to the crystalline sesquihydrate Form H1.5-2. The sesquihydrate Form 1.5-2 has a lower aqueous solubility compared to Form N-1, and concomitantly, a lower dissolution rate and lower bioavailability. One method to increase the bioavailability of compounds in a suspension is to increase the surface area of the particles in contact with the aqueous medium, which can be achieved by decreasing the particle size. However, reductions in particle size below diameters of approximately one micron requires specialized milling and dispersion techniques to prepare, stabilize, and sterilize the sub-micron suspensions. Desired is an aqueous suspension of Compound (I) in Form N-1 that has sufficient resistance to conversion to the sesquihydrate Form H1.5-2 to allow oral administration.

Applicants have surprisingly found an aqueous pharmaceutical composition suitable for providing Compound (I) with sufficient bioavailability to allow oral administration. The pharmaceutical composition is an aqueous microsuspension comprising particles of Compound (I) dispersed in an aqueous medium. The particles of Compound (I) are in the anhydrous crystalline Form N-1 and are provided with sufficient resistance to hydration to prevent and/or to hinder conversion to the sesquihydrate crystalline Form H1.5-2 in the aqueous medium prior to administration. By maintaining the particles in the anhydrous Form N-1, Compound (I) can be provided in an aqueous microsuspension with sufficient solubility, dissolution rate, and/or bioavailability to allow oral administration of Compound (I). Further, the microsuspension can be prepared by admixing dry particles of Compound (I), Form N-1, into an aqueous vehicle to provide a stable aqueous microsuspension of Compound (I), Form N-1, and thus does not require specialized milling and preparation techniques.

The microsuspension comprises particles of Compound (I) in Form N-1, wherein said particles have a particle diameter, as characterized by a $D_{90}$ value, in the range of from 1 to 50 microns, preferably in the range of from 1 to 30 microns, and more preferably, in the range of from 1 to 20 microns. Particle size analysis to determine $D_{90}$ values can be conducted by various techniques know in the art, such as, for example, techniques based on light scattering and image analysis. The concentration of particles of Compound (I) in Form N-1 of the microsuspension can be in the range of from 0.1 to 50 mg/mL, preferably, in the range of from 1 to 40 mg/mL, and more preferably, in the range of from 2 to 30 mg/mL. Examples include microsuspensions having concentrations of 2 mg/mL, 5 mg/mL, 10 mg/mL, and 20 mg/mL.

The aqueous medium of the microsuspension comprises water and optionally other water miscible solvents. Typically, the aqueous medium comprises at least 90 weight %, preferably at least 95 weight %, and more preferably, at least 99 weight % water, based on the weight of the aqueous medium. In one embodiment, the aqueous medium is substantially free of other water miscible solvents, and comprises, for example, at least 99.8 weight %, preferably, at least 99.9 weight %, and more preferably 99.95 weight % water, based on the weight of the aqueous medium.

The microsuspension also comprises a stabilizer to minimize or prevent the conversion of the N-1 Form to the sesquihydrate Form H1.5-2 in the aqueous medium. The stabilizer is dissolved in the aqueous medium used for the preparation of the microsuspension of Compound (I). Examples of suitable stabilizers include cellulose ether polymers, such as, hydroxy propyl methyl cellulose (HPMC), methyl cellulose (MC), and hydroxy propyl cellulose (HPC). Suitable amounts of the stabilizer in the microsuspension include 0.01% to 5% w/v; 0.05% to 5% w/v; and 0.1% to 4% w/v. In one embodiment, the stabilizer is partly or completely disposed on the particles of Compound (I).

In one embodiment, the microsuspension comprises particles of Compound (I) in Form N-1 are dispersed in an aqueous medium; said particles have a diameter ($D_{90}$) in the range of from 1 to 30 microns; and a stabilizer selected from a cellulose ether polymer; wherein the stabilizer is disposed on the particles. Examples of cellulose ether polymers include hydroxypropyl cellulose, hydroxypropyl methyl cellulose, and/or methyl cellulose.

The microsuspension can optionally comprises a surfactant to enhance the wetting of the solid particles during reconstitution of microsuspension. Suitable surfactants include cationic, anionic, and nonionic surfactants. One surfactant or suitable mixture of surfactants may be employed in the microsuspension. Specific examples of suitable surfactants include, but are not limited to, sorbitan esters such as polyoxyethylene (20) sorbitan monooleate, sodium alkyl sulfates such as sodium lauryl sulfate, and/or polyoxyethylene-polyoxypropylene-polyoxyethylene triblock copolymers such as PLURONIC® surfactants (ICI Americas, Delaware). The microsuspension may comprise from 0.01 to 2% w/v surfactant, preferably from 0.05 to 2% w/v surfactant, and more preferably, from 0.1 to 2% w/v surfactant, based on the volume of the microsuspension.

The microsuspension can optionally comprise a suspending agent to minimize or prevent agglomeration and/or precipitation of the particles of Compound (I). Suitable suspending agents include microcrystalline cellulose, such as, for example, AVICEL® PH 101, PH 103, PH 105, and PH 200 microcrystalline cellulose (FMC Corporation, Delaware). One or more suspending agent may be employed in the microsuspension. The microsuspension may comprise an amount of suspending agent in the range of from 0.1 to 5% w/v, preferably from 0.2 to 4% w/v, and more preferably, from 0.2 to 3%, based on the volume of the microsuspension.

The microsuspension can optionally comprise other additives and/or formulation adjuvants. Examples includes flavoring agents and sweeteners such as sorbitol, mannitol, aspartame, sucrose, and other commercially available sweeteners. One sweetener is Simple Syrup, a solution of sucrose in water used in pharmaceutical formulations. Other additives include, buffers such as pharmaceutically acceptable weak acids, weak bases, or mixtures thereof. Preferred buffers are water soluble materials such as phosphoric acid, acetic acid, their salts, or mixtures thereof, which can be use maintain a pH in the range of 5-7 in the microsuspension. Also, preservatives may be added, such as methyl or propyl parabens, or mixtures thereof.

The microsuspension can be prepared by adding the particles of Compound (I), Form N-1, with a pharmaceutical vehicle comprising the aqueous medium, one or more stabilizer, one or more surfactant, one or more suspending agent, and optionally, other additives. Various techniques such as shaking, mixing, vortexing, and/or sonicating can be employed to disperse the particles of Compound (I), Form N-1 into the vehicle.

In one embodiment, the microsuspension is provided comprising:
  a) from 0.1 to 5% (w/v) stabilizer;
  b) from 0.1 to 5% (w/v) microcrystalline cellulose;
  c) from 0.01 to 2% (w/v) sorbitan ester, sodium lauryl sulfate, dodecyl sulfate, and/or polyoxyethylene-polyoxypropylene-polyoxyethylene block copolymer; and
  d) from 1 to 40% (w/v) sweetener.

For example, in the present embodiment, the stabilizer may be selected from hydroxypropyl cellulose, hydroxypropyl methyl cellulose, and/or methyl cellulose.

Tablet Pharmaceutical Composition Comprising Form N-1 of Compound (I)

The neat N-1 Form of Compound (I) has the potential to convert to the sesquihydrate Form H1.5-2 in aqueous solution or under high humidity conditions. Solid pharmaceutical compositions comprising Form N-1 of Compound (I) require sufficient physical stability to resistance the change of crystalline form during storage, especially at high humidity storage conditions. Further, the solid pharmaceutical composition must undergo rapid disintegration and/or dissolution upon oral administration.

Applicants have surprisingly found a tablet pharmaceutical composition comprising Compound (I) in crystalline Form N-1 that has sufficient physical stability and adequate disintegration and dissolution upon administration to a patient. The tablet comprises micronized particles of Compound (I) in Form N-1; a stabilizer; a disintegrant, fillers, and optionally, other adjuvants, such as glidants and/or lubricants. The stabilizer may also bind the components of the tablet together.

Suitable processes to prepare the tablet include a wet granulation process. The wet granulation process includes a step of incorporating the stabilizer into the aqueous granulating fluid which aids in maintaining Compound (I) in anhydrous Form N-1 during processing. The stabilizer may be added as a solution or a foam. The incorporation of the stabilizer into the formulation improves the stability of the anhydrous N-1 form in the tablet, including storage of the tablet under accelerated storage conditions.

The tablet comprises particles of Compound (I) in Form N-1, wherein said particles have a particle diameter, as characterized by a $D_{90}$ value, in the range of from 1 to 50 microns, preferably in the range of from 1 to 30 microns, and more preferably, in the range of from 1 to 20 microns. The micronized particles of Compound (I) can be prepared by various techniques known in the art, including, for example, jet milling and impact milling.

In one embodiment, the tablet comprises particles of Compound (I) in Form N-1, wherein said particles have a particle diameter, as characterized by a $D_{90}$ value, in the range of from 1 to 50 microns, preferably in the range of from 1 to 30 microns, and more preferably, in the range of from 1 to 20 microns; and stabilizer is disposed on the particles. Examples of suitable stabilizers, which can also bind the tablet together include hydroxy propyl methyl cellulose (HPMC), methyl cellulose (MC), and hydroxy propyl cellulose (HPC). The stabilizer is disposed on the particles to prevent or provide resistance to conversion of Form N-1 to another form, including the sesquihydrate form H1.5-1.

In one embodiment, the tablet comprises: (i) from 10 to 50 weight %, preferably from 15 to 25 weight %, Compound (I) in Form N-1; (ii) from 2 to 12 weight %, preferably from 5 to 9 weight % disintegrant; (iii) from 1 to 7 weight %, preferably from 3 to 5 weight %, stabilizer; (iv) from 28 to 87 weight %, preferably, from 59 to 77 weight %, filler; (v) 0.1 to 1.5 weight %, preferably from 0.3 to 0.9 weight %, lubricant; and (vi) from 0.1 to 1.5 weight %, preferably, from 0.2 to 0.6 weight % glidant, based on the total weight of the tablet, wherein Compound (I) in Form N-1 is provided as particles having a particle diameter, as characterized by a $D_{90}$ value, in the range of from 5 to 50 microns, preferably in the range of from 1 to 30 microns, and more preferably, in the range of from 1 to 20 microns; and said stabilizer is disposed on said particles of Form N-1. Suitable stabilizer, which also binds the tablet together, include hydroxypropyl methyl cellulose (HPMC), methyl cellulose (MC), and hydroxypropyl cellulose (HPC). Suitable fillers include microcrystalline cellulose, mannitol, lactose, starch, sucrose, glucose, dicalcium phosphate, calcium sulfate, calcium silicate, and sorbitol. Suitable disintegrants include croscarmellose sodium, starch, methyl cellulose, crospovidone, and sodium starch glycolate. Suitable glidants include colloidal silicon dioxide, precipitated silicon dioxide, silica, and talc. Suitable lubricants include magnesium stearate, sodium oleate, sodium stearate, sodium fumarate, sodium benzoate, and sodium acetate. The tablet can be formulated at different strengths; for example, 25 mg, 50 mg, and 100 mg of Compound (I) in Form N-1.

In a further embodiment, the tablet comprises: (i) 20 weight % Compound (I) in Form N-1; (ii) 7 weight % croscarmellose sodium; (iii) 4 weight % hydroxypropyl cellulose; (iv) 68 weight % microcrystalline cellulose; (v) 0.6 weight % magnesium stearate; and (vi) 0.4 weight % silicon dioxide; based on the total weight of the tablet.

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235 (1993); Matsumato et al., *Crit. Rev. Oncog.*, 3:27-54 (1992); and Stoker et al., *Nature*, 327:239-242 (1987)). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell*, 67:901-908 (1991)), and promotion of invasion (Stella et al., *Int. J. Biochem. Cell Biol.*, 12:1357-1362 (1999) and Stuart et al., *Int. J. Exp. Path.*, 81:17-30 (2000)), all critical processes underlying metastasis. HGF has also been reported to promote angiogenesis (Bussolino et al., *J. Cell Biol.*, 119:629-641 (1992)). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA*, 84:6379-6383 (1987) and Bottaro et al., *Science*, 251:802-804 (1991)). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene*, 19:5582-5589 (2000)). These include the p85 subunit of the PI3-kinase, phospholipase Cγ (Gaul et al., *Oncogene*, 19:1509-1518 (2000)), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J Cell Biol.*, 149:1419-1432 (2000); Bardelli, et al., *Oncogene*, 18:1139-1146 (1999) and Sachs et al., *J. Cell Biol.*, 150:1375-1384 (2000)). Activation of other signaling molecules has been reported in HGF stimulated cells, most notably Ras, MAP kinases, STATs, ERK-1, -2 and FAK (Tanimura et al., *Oncogene*, 17:57-65 (1998); Lai et al., *J. Biol. Chem.*, 275:7474-7480 (2000) and Furge et al., *Oncogene*, 19:5582-5589 (2000)). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-526 (1999)). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-7355 (2003); Lee et al., *Oncogene*, 19:4947-4953 (2000) and Direnzo et al., *Clin. Cancer Res.*, 1:147-154 (1995)). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al., *Cancer Res.*, 55:1963-1970 (1995); Rong et al., *Cancer Res.*, 53:5355-5360 (1993); Kenworthy et al., *Br. J. Cancer*, 66:243-247 (1992) and Scarpino et al., *J. Pathology*, 189:570-575 (1999)). TPR-Met (an activated form similar to BCR/Abl in CML) has been described and identified in human gastric carcinoma (*Proc. Natl. Acad. Sci.*, 88:4892-4896 (1991)). In patients with invasive breast carcinoma and in a recent study in non small cell lung cancer patients, expression of either the receptor or ligand is a predictor of decreased survival, further linking Met to tumor progression (Camp et al., *Cancer*, 86:2259-2265 (1999) and Masuya et al., *Br. J. Cancer*, 90:1555-1562 (2004)). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *Proc. Natl. Acad. Sci.*, 94:701-706 (1997)) and an amplified/overexpressed Met spontaneously transforms NIH-3T3 cells (Cooper et al., *EMBO J.*, 5:2623-2628 (1986)).

Biological agents, such as ribozymes, antibodies and antisense RNA targeting either HGF or Met have been shown to inhibit tumorigenesis (Stabile et al., *Gene Therapy*, 11:325-335 (2004); Jiang et al., *Clin. Cancer Res.*, 9:4274-4281 (2003) and Genentech, U.S. Pat. No. 6,214,344 (2001)). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

Compound (I) is useful for the treatment of cancer, for example, cancers dependent upon Met activation. Met activation is regulated by gene amplification, an activated Met mutation and/or HGF stimulation. Thus, the treatment comprises administering to the patient Compound (I) or a pharmaceutically acceptable salt. It has been found that Compound (I) is especially useful for treating cancer because of increased potency over known Met kinase inhibitors.

In one embodiment, a method is provided for treating cancer comprising administering Compound (I) to a mammal in need thereof, wherein Compound (I) is in crystalline Form N-1. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gallbladder cancer, prostate cancer, thyroid cancer, osteosarcoma, rhabdomyosarcoma, malignant fibrous histiocytoma (MFH), fibrosarcoma, glioblastomas/astrocytomas, melanoma, and mesothelioma. Preferably, the method of this embodiment is used to treat lung cancer, head and neck cancer, gastric cancer, or bladder cancer. Preferably, a therapeutically effective amount of Compound (I), wherein Compound (I) is in a crystalline Form N-1, is administered.

In one embodiment, methods are provided for treating cancer in a patient wherein the cancer is dependent upon Met activation, wherein the Met activation is regulated by gene amplification, an activated Met mutation, and/or HGF stimulation, comprising administering to the patient in need thereof a therapeutically effective amount of Compound (I), wherein Compound (I) is in a crystalline Form N-1.

In another embodiment, the method for treating at least cancer involves providing administering Form N-1 of Compound (I), wherein Form N-1 is substantially pure.

The amount of Compound (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, Compound (I) may be administered in combination with other anti-cancer treatments useful in the treatment of cancer or other proliferative diseases. The invention herein further comprises use of Form N-1 of Compound (I) in preparing medicaments for the treatment of cancer, and/or it comprises the packaging of Form N-1 of Compound (I) herein together with instructions that the compound be used in combination with other anti-cancer or cytotoxic agents and treatments for the treatment of cancer. The present invention further comprises combinations of Form N-1 of Compound (I) and one or more additional agents in kit form, e.g., where they are packaged together or placed in separate packages to be sold together as a kit, or where they are packaged to be formulated together.

Compound (I) can be formulated or co-administered with other therapeutic agents that are selected for their particular usefulness in addressing side effects associated with the aforementioned conditions. For example, Compound (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/antiestrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with Compound (I), can be used, for example, in those amounts indicated in the Physicians' Desk Reference (PDR) or as otherwise determined by one of ordinary skill in the art.

In another embodiment, Form N-1 of Compound (I) is used to treat lung cancer, head and neck cancer, gastric cancer, and/or bladder cancer.

In one embodiment, the patient is an animal.

In another embodiment, the patient is a mammalian species including, but not limited to, for example, humans and domestic animals, such as, for example, dogs, cats, and horses.

In one embodiment, the present invention provides Form N-1 of Compound (I) for use in therapy.

In one embodiment, the use of Form N-1 of Compound (I) in the manufacture of a medicament for the treatment of cancer is provided. Preferably, the cancer is bladder cancer, breast cancer, colorectal cancer, gastric cancer, head and neck cancer, kidney cancer, liver cancer, lung cancer, ovarian cancer, pancreas/gallbladder cancer, prostate cancer, thyroid cancer, osteosarcoma, rhabdomyosarcoma, melanoma, glioblastomas/astrocytomas, MFH/fibrosarcoma, or mesothelioma.

In one embodiment, the use of Form N-1 of Compound (I) in the manufacture of a medicament for the treatment of cancer is provided. Preferably, the cancer is bladder cancer, breast cancer, colorectal cancer, gastric cancer, head and neck cancer, kidney cancer, liver cancer, lung cancer, ovarian cancer, pancreas/gallbladder cancer, prostate cancer, thyroid cancer, osteosarcoma, rhabdomyosarcoma, melanoma, glioblastomas/astrocytomas, MFH/fibrosarcoma, or mesothelioma.

Methods of Preparation and Characterization

Crystalline forms may be prepared by a variety of methods, including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline forms from a solvent mixture include, but are not limited to, for example, evaporation of the solvent; decreasing the temperature of the solvent mixture; crystal seeding a supersaturated solvent mixture of the compound and/or a salt from thereof; freeze drying the solvent mixture; and adding antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Byrn, S. R. et al., *Solid-State Chemistry of Drugs*, 2nd Edition, SSCI, West Lafayette, Ind. (1999).

In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the compound in the solution and precipitate the formation of crystals. An antisolvent is a solvent in which a compound has low solubility.

In one method that can be used in preparing crystals, a compound is suspended and/or stirred in a suitable solvent to afford a slurry, which may be heated to promote dissolution. The term "slurry", as used herein, means a saturated solution of the compound, wherein such solution may contain an additional amount of compound to afford a heterogeneous mixture of compound and solvent at a given temperature.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in Mullin, J. W. et al., "Programmed Cooling of Batch Crystallizers," *Chemical Engineering Science*, 26:369-377 (1971). In general, seeds of small size are needed to effectively control the growth of crystals in the batch. Seeds of small size may be generated by sieving, milling, or micronizing large crystals, or by microcrystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product washed with a suitable solvent, such as, for example, cold recrystallization solvent. After being washed, the product may be dried under a nitrogen purge to afford the desired crystalline form. The product may be analyzed by a suitable spectroscopic or analytical technique including, but not limited to, for example, solid state nuclear magnetic resonance; differential scanning calorimetry (DSC); and powder x-ray diffraction (PXRD) to assure the preferred crystalline form of the compound has been formed. The resulting crystalline form may be produced in an amount greater than about 70 wt. % isolated yield, based on the weight of the compound originally employed in the crystallization procedure, and preferably greater than about 90 wt. % isolated yield. Optionally, the product may be delumped by being comilled or passed through a mesh screen.

Crystalline forms of Compound (I) including, but not limited to, for example, the Forms described herein, may be prepared directly from the reaction medium produced via the final process step employed in preparing Compound (I). For example, crystalline form(s) of Compound (I) could be produced by employing a solvent or a mixture of solvents in the final process step employed in preparing Compound (I). Alternatively, crystalline forms of Compound (I) may be obtained by distillation or solvent addition techniques. Suitable solvents for this purpose include, but are not limited to, for example, the aforementioned nonpolar and polar solvents, wherein polar solvents include, but are not limited to, for example, protic polar solvents, such as, for example, alcohols and aprotic polar solvents, such as, for example, ketones.

The presence of more than one crystalline form and/or polymorph in a sample may be determined by techniques, including, but not limited to, for example, PXRD and solid state nuclear magnetic resonance spectroscopy. For example, the presence of extra peaks when an experimentally measured PXRD pattern is compared to a simulated PXRD pattern may indicate more than one crystalline form and/or polymorph in the sample. The simulated PXRD may be calculated from single crystal x-ray data. See, for example, Smith, D. K., "A FORTRAN Program for Calculating X-Ray Powder Diffraction Patterns," Lawrence Radiation Laboratory, Livermore, Calif., UCRL-7196 (April 1963).

Crystalline forms of Compound (I), including, but not limited to, those described herein according to the invention may be characterized using a variety of techniques well known to person(s) of ordinary skill in the art. For example, the single x-ray diffraction technique may, under standardized operating conditions and temperatures, be used to characterize and distinguish crystalline form(s) of Compound (I). Such characterization may, for example, be based on unit cell measurements of a single crystal of the desired form at a fixed analytical temperature. The approximate unit cell dimensions in Angstroms (Å), as well as the crystalline cell volume, space group, molecules per cell, and crystal density may be measured, for example, at a sample temperature of 25° C. A detailed description of unit cells is provided in Stout et al., Chapter 3, *X-Ray Structure Determination: A Practical Guide*, Macmillan Co., New York (1968), which is hereby incorporated herein by reference.

Additionally, the unique spatial arrangement of atoms in a crystalline lattice may be characterized according to the observed fractional atomic coordinates of such atoms.

Another means of characterizing the crystalline structure of the subject form is by PXRD analysis, the actual diffraction profile of such form is compared to a simulated profile representing pure powder material. Preferably, the actual and simulated profiles are both run at the same analytical temperature, and the subsequent measurements characterized as a series of 2θ values (usually four or more).

Other means of characterizing a crystalline form that may be used include, but are not limited to, for example, solid state nuclear magnetic resonance (NMR); DSC; thermography; gross examination of the crystalline or amorphous morphology; and combinations thereof.

At least one crystalline form of Compound (I) described herein was analyzed using at least one of the testing methods described hereinbelow.

Single Crystal X-Ray Measurements

Data was collected with a Bruker-Nonius CAD4 serial diffractometer (Bruker AXS, Inc., Madison, Wis.). Unit cell parameters were obtained through least-squares analysis of the experimental diffractometer settings of 25 high-angle reflections. Intensities were measured using CuKα radiation ($\lambda$=1.5418 Å) at a constant temperature with the θ-2θ variable scan technique and were corrected only for Lorentz-polarization factors. Background counts were collected at the extremes of the scan for half of the time of the scan. Alternately, single crystal data was collected with a Bruker-Nonius Kappa CCD 2000 system using CuKα radiation ($\lambda$=1.5418 Å). Indexing and processing of the measured intensity data were carried out with the HKL2000 software package (Otwinowski, Z. et al., *Macromolecular Crystallography*, Carter, W. C., Jr. et al., eds., Academic Press, NY (1997)) in the Collect program suite (Collect: Data collection software, R. Hooft, Nonius B. V., 1998). When indicated, crystals were cooled in the cold stream of an Oxford Cryosystems Cryostream Cooler (Oxford Cryosystems, Inc., Devens, Mass.) during data collection.

The structures were solved by direct methods and refined on the basis of observed reflections using either the SDP software package (SDP Structure Determination Package, Enraf-Nonius, Bohemia, N.Y.) with minor local modifications or the crystallographic package maXus (maXus Solution and Refinement Software Suite: S. Mackay, C. J. Gilmore, C. Edwards, M. Tremayne, N. Stewart, and K. Shankland).

The derived atomic parameters (coordinates and temperature factors) were refined through full matrix least-squares. The function minimized in the refinements was $\Sigma_w(|F_o|-|F_c|)^2$. R is defined as $\Sigma\|F_o|-|F_c\|/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

Simulated PXRD patterns were generated from the single crystal atomic parameters at the data collection temperature, unless noted otherwise. (Yin, S. et al., *American Pharmaceutical Review*, 6(2):80 (2003)).

Powder X-Ray Diffraction (PXRD) Measurements—Method A

About 200 mg of the sample was packed by the backloading method into a Philips PXRD sample holder. The sample holder was transferred to a Philips MPD unit (45 KV, 40 mA, CuKα), and the data was subsequently collected at room temperature in the 2 to 32 2-theta range (continuous scanning mode, scanning rate 0.03 degrees/sec., auto divergence and anti scatter slits, receiving slit: 0.2 mm, sample spinner: ON)

Powder X-Ray Diffraction Measurements—Method B

PXRD data was obtained using a Bruker C2 GADDS. The radiation was CuKα (40 KV, 50 mA). The sample-detector distance was 15 cm. Powder samples were placed in sealed glass capillaries of 1 mm or less in diameter, and the capillary was rotated during data collection. Data were collected for $3\leq2\theta\leq35°$ with a sample exposure time of at least about 1000 seconds. The resulting two-dimensional diffraction arcs were integrated to create a traditional 1-dimensional PXRD pattern with a step size of 0.02 degrees 2θ in the range of 3 to 35 degrees 2θ.

Differential Scanning Calorimetry (DSC) (Open Pan)

Differential scanning calorimetry (DSC) was conducted for each crystalline form using a TA INSTRUMENTS® model Q1000. For each analysis, the DSC cell/sample chamber was purged with 100 ml/min of ultra-high purity nitrogen gas. The instrument was calibrated with high purity indium. The heating rate was 10° C. per minute in the temperature range between 25 and 300° C. The heat flow, which was normalized by sample weight, was plotted versus the measured sample temperature. The data were reported in units of watts/gram ("W/g"). The plot was made with the endothermic peaks pointing down.

Thermal Gravimetric Analysis (TGA) (Open Pan)

Thermal gravimetric analysis (TGA) experiments were performed in a TA INSTRUMENTS® model Q500 or 2950. The sample (about 10-30 mg) was placed in a platinum pan previously tared. The weight of the sample was measured accurately and recorded to a thousand of a milligram by the instrument The furnace was purged with nitrogen gas at 100 mL/min. Data were collected between room temperature and 300° C. at 10° C./min heating rate.

Solid State Nuclear Magnetic Resonance Spectroscopy (ss-NMR)

All solid-state C-13 NMR measurements were made with a Bruker DSX-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (Bennett, A. E. et al., *J. Chem. Phys.*, 103:6951 (1995); Metz, G. et al., *J. Magn. Reson. A*, 110:219-227 (1994)). Approximately 70 mg of sample, packed into a canister-design zirconia rotor was used for each experiment. Chemical shifts (δ) were referenced to external adamantane with the high frequency resonance being set to 38.56 ppm (Earl, W. L. et al., *J. Magn. Reson.*, 48:35-54 (1982)).

EXAMPLES

Example 1

Neat Form N-1

A solution was prepared by mixing 35 g Compound (I) into 368 mL THF and 245 mL ethanol (200 proof) and heating the resulting slurry to 65° C. until Compound (I) was fully solubilized. The solution was polish filtered at a temperature in the range of 55-65° C. The filtrate was warmed to 60° C. and added to 350 mL n-heptane over 25 minutes. The resulting slurry was aged at 60° C. for 1 hour. The slurry was cooled to 5° C. over a period of one hour. The cold slurry was filtered and the crystalline off white solids were washed with 2×100 mL solution of ethanol: n-heptane (60:40 v/v). The wet cake was dried in a vacuum oven at a temperature in the range of 50-60° C. to afford 35 g of Compound (I) in Form N-1 (99.7% purity). PXRD: Method B.

Example 2

Sesquihydrate Form H1.5-2

Compound (I) was suspended in water (200 mL) and heated to 96° C. with stirring under nitrogen for 2 hours. The solid stayed at the bottom when agitation was stopped. The solid material was allowed to aged for 5 hours at room temperature. The solid was collected by filtration, rinsed with water (2×10 mL), and air suction dried for 4 hours to afford 2.66 g (78%, >98AP). PXRD: Method B.

Example 3

Monohydrate Hydrochloric Acid Salt Form H-1

A solution was prepared containing approximately 30 mg of Compound (I) in a sufficient amount of dimethylacetamide to fully dissolve the compound. Next, approximately 0.5 ml of 1N aqueous hydrochloric acid was added. The solution was mixed and isopropyl acetate was added dropwise until the solution became cloudy. The solution was allowed to sit overnight. The resulting slurry was filtered and the crystalline solids were washed with isopropyl acetate. PXRD: Method B.

Example 4

Neat Hydrochloric Acid Salt Form N-2

A solution was prepared by adding 100 mg of Compound (I) to 5.6 mL of dichloromethane at 40° C. Next, 16.4 µL of 37% HCl solution was added. The solution was stirred at 40° C. for 1 hour, and then cooled from 40° C. to 20° C. over a period of one hour. The resulting slurry was filtered. The wet cake was washed with 0.5 mL of dichloromethane and dried in a vacuum oven at 50° C. overnight. The dry cake was added to 0.5 mL of isopropyl acetate to form a slurry. The slurry was stirred at 50° C. for 15 hours, cooled to 20° C. over a period of one hour, and stirred overnight. The slurry was filtered and the resulting wet cake was dried in a vacuum oven at 50° C. overnight to afford seed crystals of the hydrochloric acid salt Form N-2.

A solution was prepared by mixing 1 g of Compound (I) into 56 mL of dichloromethane at 40° C. Next, 100 µL of 37% HCl solution was added. To the solution was added 5 mg of seed crystals of the neat hydrochloric acid salt of Compound (I). The solution became cloudy. Next, 63.5 µL of 37% HCl solution was added to the cloudy solution. The cloudy solution was stirred for 20 minutes at 40° C., then allowed to cool from 40° C. to 20° C. over a period of 40 minutes. The resulting slurry was stirred for four hours and then filtered. The wet cake was washed with 3 mL of dichloromethane and then dried in a vacuum oven at 50° C. overnight. The dry cake weighed 0.83 g. The dry cake was reslurried in 8.3 mL of isopropyl acetate. The slurry was stirred at 50° C. for 15 hours, cooled to 20° C. over a period of an hour, and continued to be stirred overnight. The slurry was filtered. The wet cake was washed with 2.4 mL of isopropyl acetate and then dried in a vacuum over at 50° C. overnight. The dry cake weighed 0.74 g. PXRD: Method A.

Example 5

Phosphoric Acid Salt Form

A solution was prepared by adding 100 mg of Compound (I) to a mixture of 1 mL of isopropyl acetate and 0.5 mL of N-methyl pyrrolidinone at 70° C. Separately, 13.5 µL (1.0 equiv.) of 85% $H_3PO_4$ was dissolved in 0.5 mL of isopropanol at room temperature. The $H_3PO_4$ solution was added to the solution of Compound (I) in portions over a period of 30 minutes. The resulting solution was cooled from 50° C. to 20° C. over a period of 60 minutes, and allowed to stir for four days. The resulting slurry was filtered and the wet cake was washed with 0.5 mL of isopropyl acetate and dried in a vacuum oven at 50° C. overnight to afford seed crystals of the phosphoric acid salt of Compound (I).

A solution was prepared by mixing 5 g of Compound (I) into a mixture of 12 mL of dimethylacetamide and 5 mL of isopropyl acetate at 50° C. In a separate container, a phosphoric acid solution was prepared by mixing 663 µL (1.0 equiv.) of 85% $H_3PO_4$ into 12.5 mL of isopropanol at room temperature. Next, 2 mL of the phosphoric acid solution to the solution of Compound (I), followed by the addition of 50 mg of seed crystals of the phosphoric acid salt of Compound (I). The solution of Compound (I) became a slurry. Next, the remaining phosphoric acid solution was added over a period of one hour using a syringe pump. Then, 62.5 mL of isopropyl acetate was added over a period of one hour using the syringe pump. The slurry was stirred at 50° C. for 10 minutes, allowed to cool from 50° C. to 20° C. over 60 minutes. Stirring was continued for two hours. The slurry was filtered. The wet cake was washed with 20 mL of isopropyl acetate. The wet cake was dried in a vacuum over at 50° C. overnight. The resulting dried powder weighed 5.75 g. PXRD: Method B.

TABLE 5

Characteristic diffraction peak positions (degrees 2θ ± 0.2) at room temperature, based on a high quality pattern collected with a diffractometer (CuKα) with a spinning capillary with 2θ calibrated with a NIST other suitable standard

| N-1 | H1.5-2 | H-1 HCl | N-2 HCl | Phosphoric Acid Salt |
|------|--------|---------|---------|----------------------|
| 6.2  | 7.4    | 6.3     | 6.4     | 4.8  |
| 7.7  | 10.4   | 7.0     | 9.6     | 6.1  |
| 11.0 | 12.2   | 9.4     | 10.4    | 7.4  |
| 12.2 | 13.4   | 15.5    | 11.2    | 9.2  |
| 18.5 | 18.9   | 16.6    | 14.0    | 9.7  |
| 21.6 | 19.7   | 18.7    | 15.2    | 11.3 |
| 22.2 | 21.5   | 20.7    | 16.5    | 12.2 |
| 23.0 | 22.0   | 23.9    | 19.1    | 13.3 |
| —    | —      | —       | 22.0    | 16.9 |
| —    | —      | —       | —       | 22.5 |
| —    | —      | —       | —       | 23.5 |

Example 6

Preparation of a Microsuspension Containing 10 Mg Compound (I), 1% w/v Hydroxypropyl Cellulose, 1% w/v AVICEL® PH101 Microcrystalline Cellulose, 0.1% w/v TWEEN 80 Surfactant, and 25% v/v Simple Syrup NF In a first container, 1 g of hydroxypropyl cellulose was added to 50 mL of water and the resulting mixture was stirred for a period of about 2 to 3 hours using a magnetic stir bar to obtain a clear solution. In a second container, 25 mL water was added to 0.1 g TWEEN 80 surfactant and the resulting mixture was stirred for 15 min until the surfactant was dissolved. The TWEEN 80 surfactant solution was then added to the contents of the first container. Next, 25 mL of Simple Syrup NF was added to the first container. The contents of the first container was stirred for 15-20 min to form a uniform solution. Next, 1 g of AVICEL® PH 101 microcrystalline cellulose (FMC Corporation, Philadelphia, Pa.) was added and stirred for 10 min to obtain a uniform dispersion. The resulting vehicle solution comprised 1% w/v hydroxypropyl cellulose, 1% w/v AVICEL® PH101 microcrystalline cellulose, 0.1% w/v TWEEN 80 surfactant, and 25% v/v simple syrup NF.

A microsuspension of Compound (I) was prepared by adding 2 mL of the vehicle solution to 10 mg of Compound (I) while stirring continuously. The resulting mixture was swirled manually to ensure wetting of the particles of Compound (I) and then sonicated for approximately 20 min to obtain a microsuspension of Compound (I) particles.

TWEEN 80 surfactant: Polyoxyethylene (20) sorbitan monooleate (ICI Americas Inc., Delaware). AVICEL® PH101: microcrystalline cellulose (FMC Corporation, Delaware). Simple Syrup: 850 g sucrose in water, 1000 mL total volume. % w/v refers to the weight of additive in grams per volume of microsuspension in mL.

Example 7

Preparation of a Microsuspension Containing 100 Mg Compound (I), 1% w/v Hydroxypropyl Cellulose, 1% w/v AVICEL® PH101 Microcrystalline Cellulose, 0.1% w/v TWEEN 80 Surfactant, and 25% v/v Simple Syrup NF A microsuspension of Compound (I) was prepared by adding 5 mL of the vehicle of Example 6 to 100 mg of Compound (I) while stirring continuously. The resulting mixture was swirled manually to ensure wetting of the particles of Compound (I) and then sonicated for approximately 20 minutes to obtain a microsuspension of Compound (I) particles.

Example 8

Preparation of Tablets Comprising Compound (I) in Form N-1 and Microcrystalline Cellulose A 3.0% (w/w) hydroxypropyl cellulose (HPC) stabilizer-binder solution was prepared using an overhead mixer. The resulting hydroxypropyl cellulose solution stream was mixed with air stream, using a foam generator, to yield HPC foam. The solid intragranular ingredients listed in Table 6 were mixed in a 6 L capacity high shear mixer. Next, the mixed intragranular ingredients were granulated in the same mixer using the HPC foam. The granules were passed through #4 mesh screen and tray dried to a moisture content of <3% by weight. The dried granules were milled using a COMIL® fitted with ~1 mm opening screen. The extragranular colloidal silicon dioxide, croscarmellose sodium and magnesium stearate were blended in with the milled granules using a tumble mixer to provide the stock granulation for tableting. The stock granulation for tableting was used to prepare 25 mg and 100 mg strength tablets (Table 7).

TABLE 6

| Ingredient | Amount (% w/w) | Amount (g) |
|---|---|---|
| Part I. Intragranular Ingredients | | |
| Compound (I) in Form N-1 | 20.00 | 140.00 |
| Croscarmellose sodium, NF | 3.50 | 24.50 |
| Hydroxypropyl cellulose, NF (added as foam) | 1.350 | 9.45 |
| Hydroxypropyl cellulose, NF | 2.650 | 18.55 |
| Microcrystalline cellulose, NF | 68.00 | 476.00 |
| Part II. Extragranular Ingredients | | |
| Magnesium stearate, NF | 0.60 | 4.20 |
| Colloidal silicon dioxide, NF | 0.40 | 2.80 |
| Croscarmellose sodium, NF | 3.50 | 24.50 |
| Total | 100.0 | 700.0 |

TABLE 7

| Ingredient | Composition of Stock Granulation (w/w %) | Composition of 25 mg Strength Tablet (mg) | Composition of 100 mg Strength Tablet (mg) |
|---|---|---|---|
| Compound (I) in Form N-1 | 20.00 | 25.0 | 100.0 |
| Croscarmellose sodium, NF | 7.00 | 8.8 | 35.0 |
| Hydroxypropyl cellulose, NF | 4.00 | 5.0 | 20.0 |
| Microcrystalline cellulose, NF | 68.00 | 85.0 | 340.0 |
| Magnesium stearate, NF | 0.60 | 0.8 | 3.0 |
| Colloidal silicon dioxide, NF | 0.40 | 0.5 | 2.0 |
| Total | 100.00 | 125.0 | 500.0 |

Example 9

Preparation of Tablets Comprising Compound (I) in Form N-1 and Microcrystalline Cellulose/Mannitol The tablets were prepared according to the general procedure described in Example 8 using the ingredients in Table 8.

TABLE 8

| Ingredient | Amount (% w/w) | Amount (g) |
|---|---|---|
| Part I. Intragranular Ingredients | | |
| Compound (I) in Form N-1 | 20.00 | 140.00 |
| Croscarmellose sodium, NF | 3.50 | 24.50 |
| Mannitol, USP | 20.00 | 140.00 |
| Hydroxypropyl cellulose, NF (added as foam) | 1.350 | 9.45 |
| Hydroxypropyl cellulose, NF | 2.650 | 18.55 |
| Microcrystalline cellulose, NF | 47.85 | 334.95 |
| Part II. Extragranular Ingredients | | |
| Magnesium stearate, NF | 0.75 | 5.25 |
| Colloidal silicon dioxide, NF | 0.40 | 2.80 |
| Croscarmellose sodium, NF | 3.50 | 24.50 |
| Total | 100.0 | 700.0 |

TABLE 9

| Ingredient | Composition of Stock Granulation (w/w %) | Composition of 25 mg Strength Tablet (mg) | Composition of 100 mg Strength Tablet (mg) |
|---|---|---|---|
| Compound (I) in Form N-1 | 20.0 | 25.0 | 100.0 |
| Croscarmellose sodium, NF | 7.0 | 8.8 | 35.0 |
| Hydroxypropyl cellulose, NF | 4.0 | 5.0 | 20.0 |
| Microcrystalline cellulose, NF | 47.85 | 59.8 | 239.3 |
| Mannitol, USP | 20.00 | 25.0 | 100.0 |
| Magnesium stearate, NF | 0.6 | 0.8 | 3.0 |
| Colloidal silicon dioxide, NF | 0.4 | 0.5 | 2.0 |
| Total | 100.0 | 125.0 | 500.0 |

Example 10

Preparation of Tablets Comprising Compound (I) in Form N-1 Manufactured Via Wet Granulation Process An aqueous granulating solution was prepared by dissolving 2.5% w/w of hydroxypropyl cellulose and 10% w/w of Poloxamer-188 surfactant in water, using an overhead mixer. The solid intragranular ingredients listed in Table 10 were mixed in a 1 L capacity high shear mixer. Next, the mixed intragranular ingredients were granulated in the same mixer using the granulating solution. The granules were tray dried to a moisture content of <3% by weight. The dried granules were hand screened through a #20 mesh screen. The extragranular colloidal silicon dioxide, croscarmellose sodium, and magnesium stearate were blended in with the milled granules using a tumble mixer to provide the stock granulation for tableting. The stock granulation for tableting was used to prepare 100 mg strength tablets.

TABLE 10

| Ingredient | Amount (% w/w) | Amount (g) |
|---|---|---|
| Part I. Intragranular Ingredients | | |
| Compound (I) in Form N-1 | 40.00 | 40.00 |
| Croscarmellose sodium, NF | 5.00 | 5.00 |
| Hydroxypropyl cellulose, NF (added as solution) | 0.62 | 0.62 |
| Poloxamer-188 surfactant (added as solution) | 2.50 | 2.50 |
| Hydroxypropyl cellulose, NF | 3.38 | 3.38 |
| Microcrystalline cellulose, NF | 42.90 | 42.90 |
| Part II. Extragranular Ingredients | | |
| Magnesium stearate, NF | 0.30 | 0.30 |
| Colloidal silicon dioxide, NF | 0.30 | 0.30 |
| Croscarmellose sodium, NF | 5.00 | 5.00 |
| Total | 100.0 | 100.0 |

Comparative Example 11

Preparation of Tablets Comprising Compound (I) in Form N-1 Manufactured Via Dry Granulation Process The solid intragranular ingredients listed in Table 11 were mixed in a 1 L capacity high shear mixer. Next, the mixed intragranular ingredients were slugged using a F-press equipped with a ¾ inch flat face slugging tool. The slugs were hand screened through a #4 and then a #20 mesh screen. The extragranular colloidal silicon dioxide, croscarmellose sodium, and magnesium stearate were blended in with the milled granules using a tumble mixer to provide the stock granulation for tableting. The stock granulation for tableting was used to prepare 100 mg strength tablets.

TABLE 11

| Ingredient | Amount (% w/w) | Amount (g) |
|---|---|---|
| Part I. Intragranular Ingredients | | |
| Compound (I) in Form N-1 | 40.00 | 40.00 |
| Croscarmellose sodium, NF | 5.00 | 5.00 |
| Hydroxypropyl cellulose, NF | 4.00 | 4.00 |
| Poloxamer-188 surfactant (Micro 68 MP grade) | 3.00 | 3.00 |
| Magnesium stearate, NF | 0.30 | 0.30 |
| Microcrystalline cellulose, NF | 42.00 | 42.00 |
| Colloidal silicon dioxide, NF | 0.25 | 0.25 |
| Part II. Extragranular Ingredients | | |
| Magnesium stearate, NF | 0.20 | 0.20 |
| Colloidal silicon dioxide, NF | 0.25 | 0.25 |
| Croscarmellose sodium, NF | 5.00 | 5.00 |
| Total | 100.0 | 100.0 |

Example 12

Stability of Microsuspensions

Microsuspension were prepared with micronized particles of Compound (I) in Form N-1 (anhydrous) using various polymers at a concentration of 20 mg/mL of the polymer, based on the microsuspension. The stability of the crystalline form was evaluated after 18-24 hours using PXRD.

TABLE 12

| Polymer (20 mg/mL) | Initial Crystalline Form of Compound (I) | Crystalline Form of Compound (I) after 18-24 hours |
|---|---|---|
| Hydroxypropyl methyl cellulose | Form N-1 | Form N-1 |
| Hydroxypropyl cellulose | Form N-1 | Form N-1 |
| Methyl cellulose | Form N-1 | Form N-1 |
| Polyvinylpyrrolidone | Form N-1 | Form H1.5-2 (sesquihydrate) |

The results indicate that use of a cellulose ether polymer, such as hydroxypropyl methyl cellulose, hydroxypropyl cellulose, and methyl cellulose, delayed or prevented conversion of micron sized particles of Form N-1 of Compound (I) dispersed in an aqueous medium to the sesquihydrate Form H1.5-2. In contrast, use of polyvinylpyrrolidone did not delay or prevent conversion of micron sized particles of Form N-1 of Compound (I) dispersed in an aqueous medium to the sesquihydrate Form H1.5-2.

Example 13

Stability Studies of Tablets

The chemical stability of the 25 mg tablet of Example 9 was evaluated after accelerated storage at various temperatures and humidity conditions for periods up to one month.

TABLE 13

| | Total Impurity (%) | Potency (mg/tab) | Tablet Weight (mg) |
|---|---|---|---|
| Compound (I) - control | 0.13 | — | — |
| RT, two weeks | 0.12 | 26.1 | 127.7 |
| RT, one month | 0.12 | 25.6 | 127.3 |
| 40° C./75% RH open dish, two weeks | 0.12 | 26.4 | 132.6 |
| 40° C./75% RH open dish, one month | 0.13 | 26.0 | 133.3 |
| 40° C./75% RH closed dish, no desiccant, two weeks | 0.12 | 26.3 | 129.1 |
| 40° C./75% RH closed dish, no desiccant, one month | 0.12 | 25.8 | 129.3 |
| 40° C./75% RH closed dish, with desiccant, two weeks | 0.12 | 26.8 | 127.0 |
| 40° C./75% RH closed dish, with desiccant, one month | 0.12 | 25.7 | 127.8 |
| 50° C. closed dish, with desiccant, two weeks | 0.12 | 26.8 | 128.2 |
| 50° C. closed dish, with desiccant, one month | 0.13 | 25.4 | 127.1 |

RT: room temperature;
RH: relative humidity

The results in Table 13 show that the tablets have acceptable chemical stability.

The physical stability of the crystalline N-1 form of Compound (I) in the 100 mg tablets of Example 8 was evaluated under accelerated storage conditions (40° C./75% RH open) for a period of 6 weeks. Powder X-Ray Diffraction (PXRD) analysis showed Compound (I) to remain in the N-1 form, thus indicating that the tablets are resilient to form conversion under accelerated storage conditions.

The tablets of Example 10 and 11 were evaluated by PXRD under accelerated storage conditions (40° C./75% RH open) for a period of up to 3 months. The tablets manufactured via the wet granulation process (Example 10) contained the predominantly the N-1 form at the 24 hr and the 3 month time points. In contrast, the tablets manufactured via the dry granulation process (Example 11) showed evidence of form conversion to H1.5-2 within 24 hours, and nearly complete form conversion to H1.5-2 by 3 months. The data indicated that the disposition of the stabilizer within the tablet matrix is important for maintaining the N-1 form during storage.

TABLE 14

| | Crystalline Form of Compound (I) after 1 day | Crystalline Form of Compound (I) after 3 months |
|---|---|---|
| Tablets from Example 10 [Wet granulation] | Form N-1 | Form N-1 |
| Tablets from Example 11 [Dry Granulation] | Form N-1 + Form H1.5-2 | Form H1.5-2 |

The dissolution times of the 100 mg tablets of Example 9 was evaluated before and after storage at various conditions for a period of one month. The dissolution media was 0.1N HCl solution. Table 15 reports the average dissolution time for 3 tablets at each storage condition.

TABLE 15

| | Weight % of Tablet Dissolved | | | | | |
|---|---|---|---|---|---|---|
| Storage Conditions | 10 min | 20 min | 30 min | 45 min | 60 min | 90 min |
| Control (initial) | 102% | 103% | 103% | 104% | 104% | 104% |
| 1 month@40° C./75% RH open | 102% | 104% | 104% | 104% | 104% | 104% |

TABLE 15-continued

| | Weight % of Tablet Dissolved | | | | | |
|---|---|---|---|---|---|---|
| Storage Conditions | 10 min | 20 min | 30 min | 45 min | 60 min | 90 min |
| 1 month@40° C./75% RH closed with desiccant | 104% | 104% | 105% | 104% | 104% | 104% |

The results in Table 15 show that the tablets have acceptable dissolution times after storage under accelerated conditions.

Example 14

Pharmacokinetic Studies

The microsuspension of Example 7, tablets, and hard gelatin capsules containing the phosphate salt of Compound (I) were dosed orally at 10 mg/kg in dogs pretreated with pentagastrin. The resulting exposures were compared to an absolute bioavailability calculated by comparison to an IV dose in the same animals.

TABLE 16

| Treatment | Particle Diameter $D_{90}$ (micron) | Subject No. | PK Parameters | | |
|---|---|---|---|---|---|
| | | | $AUC_t$ ($\mu M * h$) | $C_{max}$ ($\mu Molar$) | $T_{max}$ (h) |
| Microsuspension Form N-1 | 10 | 1 | 92.5 | 20.5 | 2.0 |
| | | 2 | 90.0 | 16.4 | 2.0 |
| | | 3 | 168.5 | 34.5 | 2.0 |
| | | Average | 117.0 | 23.8 | 2.0 |
| | | Stdev | 44.6 | 9.5 | 0.0 |
| Microsuspension Form H1.5-1 | 2 | 1 | 49.5 | 10.9 | 2 |
| | | 2 | 34.5 | 8.1 | 1 |
| | | Average | 42 | 9.5 | 1.5 |
| Tablet# Form N-1 | 12 | 1 | 133.4 | 24.2 | 6.0 |
| | | 2 | 36.2 | 5.6 | 2.0 |
| | | 3 | 75.1 | 13.1 | 1.0 |
| | | Average | 81.5 | 14.3 | 3.0 |
| | | Stdev | 48.9 | 9.3 | 2.6 |
| Tablet## Form N-1 | 12 | 1 | 54.1 | 11.1 | 2.0 |
| | | 2 | 176.8 | 29.8 | 2.0 |
| | | 3 | 222.8 | 48.4 | 2.0 |
| | | Average | 151.2 | 29.8 | 2.0 |
| | | Stdev | 87.2 | 18.6 | 0.0 |
| Capsule* Phosphate Salt (I) | | 1 | 203.4 | 35.7 | 2.0 |
| | | 2 | 86.3 | 17.0 | 2.0 |
| | | 3 | 170.6 | 34.5 | 2.0 |
| | | Average | 153.4 | 29.1 | 2.0 |
| | | Stdev | 60.4 | 10.5 | 0.0 |
| Capsule* Phosphate Salt (II) | | 1 | 125.7 | 23.8 | 2.0 |
| | | 2 | 162.2 | 38.2 | 2.0 |
| | | 3 | 47.8 | 9.8 | 2.0 |
| | | Average | 111.9 | 23.9 | 2.0 |
| | | Stdev | 58.4 | 14.2 | 0.0 |

*Capsules contained Compound (I) loading of 50% w/w (free base equivalent), lactose (15% w/w), microcrystalline cellulose PH 101 (24% w/w), and Poloxamer 188 (2% w/w).
Tablets of Example 10.
Tablets contained Compound (I) loading of 40% w/w, hydroxypropyl cellulose (4.0% w/w), microcrystalline cellulose (48.1% w/w), croscarmellose sodium (7.0% w/w), colloidal silicon dioxide (0.4% w/w) and magnesium stearate (0.5% w/w) and were prepared according to the general procedure described in Example 8.

The results show that the microsuspension comprising particles of Compound (I) in Form N-1 had average pharmacokinetic parameter values for $AUC_t$ and $C_{max}$ of 117.0 µM*h and 23.8 µMolar, respectively. In contrast, the microsuspension comprising particles of Compound (I) in the sesquihydrate Form H1.5-1 had average pharmacokinetic parameters values for $AUC_t$ and $C_{max}$ of 42 µM*h and 9.5 µMolar, respectively. The results indicate that the particles of Form N-1 have higher bioavailability than the particles of the sesquihydrate Form H1.5-1, even though the sesquihydrate Form H1.5-1 particles were smaller than the Form N-1 particles. Further, tablets comprising Form N-1 with a $D_{90}$ particle size of 12 µm had average pharmacokinetic parameter values greater than the values of the microsuspension comprising Form H1.5-1, indicating higher bioavailability.

Capsules were prepared comprising Compound (I), Form N-1 with two different particle sizes. The effect of particle size on the bioavailability is shown in Table 17 below.

TABLE 17

| | Compound (I), Form N-1 | |
|---|---|---|
| Particle Diameter $D_{90}$ (micron) | 10 | 70 |
| Dose | 10 mpk | 10 mpk |
| $T_{max}$ (h) | 6 ± 0 | 2 ± 0 |
| $C_{max}$ (nM) | 15 ± 2.7 | 6.9 ± 1.1 |
| AUC (nM) | 90.2 ± 5.5 | 33.3 ± 8.4 |
| Absolute Bioavailability %* | ~32 | 12 |

*compared to IV data.

The results show that Compound (I) in Form N-1 provided as particles with a $D_{90}$ particle diameter of 10 microns had an absolute bioavailability of approximately 32% compared to an absolute bioavailability of 12% for particles with a $D_{90}$ particle diameter of 70 microns.

What is claimed is:

1. A crystalline form of Compound (I):

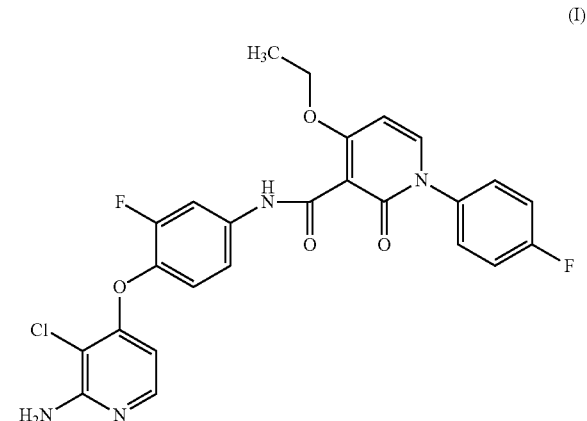

(I)

wherein said compound is a phosphoric acid salt and wherein said crystalline form of said phosphoric acid salt is characterized by one or more of the following:
 a) an observed powder x-ray diffraction pattern substantially as shown in FIG. 5; and/or
 b) four or more 2θ values selected from: 4.8±0.2, 6.1±0.2, 7.4±0.2, 9.2±0.2, 9.7±0.2, 11.3±0.2, 12.2±0.2, 13.3±0.2, 16.9±0.2, 22.5±0.2, and 23.5±0.2, wherein the PXRD pattern of the salt is obtained using a CuKα wavelength, λ=1.5418 Å and is measured at a temperature of about 25° C.

* * * * *